United States Patent
Etchenique et al.

(10) Patent No.: US 9,688,708 B2
(45) Date of Patent: Jun. 27, 2017

(54) PHOTOLABILE COMPOUNDS

(71) Applicants: The Trustees of Columbia University In The City of New York, New York, NY (US); Universidad de Buenos Aires, Buenos Aires (AR)

(72) Inventors: Roberto Etchenique, Buenos Aires (AR); Rafael Yuste, New York, NY (US); Luis Baraldo, Buenos Aires (AR)

(73) Assignees: THE TRUSTEES OF COLUMBIA UNIVERSITY IN THE CITY OF NEW YORK, New York, NY (US); Universidad de Buenos Aires, Autonoma de Buenos Aires (AR)

( * ) Notice: Subject to any disclaimer, the term of this patent is extended or adjusted under 35 U.S.C. 154(b) by 0 days.

(21) Appl. No.: 15/056,340

(22) Filed: Feb. 29, 2016

(65) Prior Publication Data

US 2016/0176907 A1  Jun. 23, 2016

Related U.S. Application Data

(60) Continuation of application No. 13/279,876, filed on Oct. 24, 2011, now Pat. No. 9,273,032, which is a division of application No. 10/585,013, filed as application No. PCT/US2004/042147 on Dec. 14, 2004, now Pat. No. 8,063,216.

(60) Provisional application No. 60/532,976, filed on Dec. 29, 2003.

(51) Int. Cl.
| | |
|---|---|
| C07F 15/00 | (2006.01) |
| A61K 31/555 | (2006.01) |
| C07D 401/14 | (2006.01) |
| C07F 15/06 | (2006.01) |
| G01N 33/50 | (2006.01) |

(52) U.S. Cl.
CPC ........ *C07F 15/0046* (2013.01); *C07D 401/14* (2013.01); *C07F 15/06* (2013.01); *G01N 33/5008* (2013.01)

(58) Field of Classification Search
USPC .............................................. 546/2; 514/188
See application file for complete search history.

(56) References Cited

U.S. PATENT DOCUMENTS

| | | | |
|---|---|---|---|
| 5,350,644 A | 9/1994 | Graetzel et al. |
| 5,393,903 A | 2/1995 | Gratzel et al. |
| 5,399,694 A | 3/1995 | Riess et al. |
| 5,463,057 A | 10/1995 | Graetzel et al. |
| 5,482,867 A | 1/1996 | Barrett et al. |
| 5,514,710 A | 5/1996 | Haugland et al. |
| 5,635,608 A | 6/1997 | Haugland et al. |
| 5,789,592 A | 8/1998 | Gratzel et al. |
| 5,872,243 A | 2/1999 | Gee et al. |
| 5,888,829 A | 3/1999 | Gee et al. |
| 6,352,824 B1 | 3/2002 | Buck, Jr. et al. |
| 6,569,544 B1 | 5/2003 | Alain et al. |
| 6,605,200 B1 | 8/2003 | Mao et al. |
| 6,750,357 B1 | 6/2004 | Chiarello et al. |
| 2002/0016472 A1 | 2/2002 | Tsien et al. |
| 2003/0198960 A1 | 10/2003 | Fan et al. |
| 2008/0176940 A1 | 7/2008 | Etchenique et al. |

FOREIGN PATENT DOCUMENTS

| | | |
|---|---|---|
| EP | 0414730 | 12/1999 |
| EP | 1178084 | 6/2002 |
| WO | WO-03/093236 | 11/2003 |
| WO | WO-2010/151879 | 12/2010 |

OTHER PUBLICATIONS

Araya, R. et al.: Two-photon optical interrogation of individual dendritic spines with caged dopamine. ACS Chem. Neurosc., vol. 4, pp. 1163-1167, 2013.*
Fino, E. et al.: RuBi-glutamate: two-photon and visible-light photoactivation of neurons and dendritic spines. Front. in Neur. Res., vol. 3, pp. 1-9, 2009.*
Zayat, L. et al.: A new inorganic photolabile protecting group for highly efficient visible light GABA uncaging. ChemBioChem, vol. 8, pp. 2035-2038, 2007.*
Adamczyk et al., "Efficient Synthesis of Rhodamine Conjugates Through the 2'-Position," J. Bioorg. Med. Chem. Lett. vol. 10, pp. 1539-1541 (2000).
Bessel et al., "Steric Ligand Effects of Six Bidentate Bipyridyl Ligands," Inorg. Chem. vol. 32, No. 25, pp. 5779-5784 (1993).
Bosnich et al., "Bis-1,10-Phenanthroline Complexes of Divalent Ruthenium," Aust. J. Chem. vol. 19, pp. 2229-2233 (1966).
Buchwald et al., "Long-term, continuous intravenous heparin administration by an implantable infusion pump in ambulatory patients with recurrent venous thrombosis," Surgery vol. 88, No. 4, pp. 507-516 (1980).
Chun-Ying et al., "Crystal Structure and Photochemistry of BIS(Bipyridine)-BIS(4-Aminopyridine)Ruthenium(II)," J. Coord. Chem. vol. 46 pp. 301-312 (1999).
European Search Report issued for corresponding EP application No. 10792793.1, mailed Dec. 5, 2012 (10 pages).
International Search Report for corresponding International Application No. PCT/US10/40220, dated Jan. 18, 2011 (1 page).
Denk, "Two-photon scanning photochemical microscopy: Mapping ligand-gated ion channel distributions," Proc. Natl. Acad. Sci. USA, vol. 91, pp. 6629-6633 (1994).
Denk et al., "Two-Photon Laser Scanning Fluorescence Microscopy," Science vol. 248, pp. 73-76 (1990).

(Continued)

*Primary Examiner* — Charanjit Aulakh
(74) *Attorney, Agent, or Firm* — Wilmer Cutler Pickering Hale and Dorr LLP

(57) ABSTRACT

The present invention describes Photolabile Compounds methods for use of the compounds. The Photolabile Compounds have a photoreleasable ligand, which can be biologically active, and which is photoreleased from the compound upon exposure to light. In one embodiment, the light is visible light, which is not detrimental to the viability of biological samples, such as cells and tissues, in which the released organic molecule is bioactive and can have a therapeutic effect.

21 Claims, 12 Drawing Sheets

(56) References Cited

OTHER PUBLICATIONS

Dodsworth et al., "Correlations between electrochemical potentials and optical charge transfer energies in ruthenium bipyridine derivatives," Chem. Phys. lett., vol. 124, pp. 152-158 (1986).
During et al., "Controlled Release of Dopamine from a Polymeric Brain Implant: In Vivo Characterization," Annals of Neurology vol. 25, No. 4, pp. 351-356 (1989).
Ellis et al., "Oxidative electropolymerization of polypyridyl complexes of ruthenium," Inorganic Chem. vol. 22 pp. 1283-1291 (1983).
Ershov et al., "Chemistry of ruthenium polypyridine complexes," Russian J. of Gen. Chem. vol. 72 pp. 1327-1338 (2002).
Fino et al., "RuBi-Glutamate: two-photon and visible-light photoactivation of neurons and dendritic spines," Frontiers in Neural Circuits vol. 3, Article 2, pp. 1-9 (2009).
Fujimoto et al., "Photonic Materials, Devices and Systems," Laser Medicine and Medical Imaging Group, RLE Progress Report 144, pp. 27-1 to 27-35 (2001).
Furuta et al., "Acyloxycoumarinylmethyl-caged cAMP, the photolabile and membrane-permeable derivative of cAMP that effectively stimulates pigment-dispersion response of melanophores," Biochem. Biophys. Res. Commun. vol. 228 pp. 193-198 (1996).
Goodson, "Dental Applications," Medical Applications of Controlled Release, Chapter 6, vol. 2, pp. 115-138 (1984).
Griffith et al., "Ruthenate-catalysed dehydrogenation of primary amines to nitriles, and crystal structure of cis-[Ru(bipy)$_2$(NH$_2$CH$_2$Ph)$_2$]-[PF$_6$]$_2$·0.5MeOH and cis-[Ru(bipy)$_2$(NCPh)$_2$][PF$_6$]$_2$CH$_2$CL$_2$," J. Chem. Soc., Dalton Trans., pp. 2819-2825 (1998).
Haugland, "Handbook of Fluorescent Probes and Research Chemicals," 6th edition, Molecular Probes 1996, table of contents (6 pages).
Howard et al., "Intacerebral drug delivery in rats with lesion-induced memory deficits" J. Neurosurg. vol. 71, pp. 105-112 (1989).
Johnson et al., "Influence of variations in the chromophoric ligand on the properties of metal-to-ligand charge-transfer excited states," Inorganic Chemistry, vol. 27, pp. 3195-3200 (1988).
Katz et al., "4-Cyanopyridine-Bridged Binuclear and Trinuclear Complexes of Ruthenium and Iron," Inorg. Chem. vol. 27, No. 10, pp. 1687-1694 (1988).
Langer et al., "Medical Applications of Controlled Release," vol. I, CRC Press Inc., Boca Raton, FL, 1984, table of contents (4 pages).
Langer, "New Methods of Drug Delivery," Science vol. 249, pp. 1527-1533 (1990).
Langer et al., "Chemical and Physical Structure of Polymers as Carriers for Controlled Release of Bioactive Agents: A Review," J. Macromol. Sci. Rev. Macromol. Chem. vol. 23, pp. 61-126 (1983).
Lebon et al., "X-ray structure, redox and spectroscopic properties of ruthenium phosphine complexes [Ru(tpy)(bpy)(PPh$_3$)]$^{2+}$ and [Ru(tpy)(bpy)(PCy$_3$)]$^{2+}$," Inorganica Chimica Acta vol. 360, No. 3, pp. 1235-1239 (2007).
Levy et al., "Inhibition of Calcification of Bioprosthetic Heart Valves by Local Controlled-Release Diphosphonate," Science vol. 228, No. 4696, pp. 190-192 (1985).
Lopez-Berestein, "Treatment of Systemic Fungal Infections with Liposomal-Amphotericin B," Liposomes in the Therapy of Infectious Disease and Cancer, Alan R. Liss, Inc., NY, pp. 317-327 (1989).
Marmion et al., "Ruthenium(IV)-Oxo Complexes: The Novel Utilization of Tertiary Pnictogen Ligands," J. Am. Chem. Soc. vol. 110, No. 5, pp. 1472-1480 (1988).
Mines et al., "Rates of heme oxidation and reduction in Ru(His33)cytochrome c at very high driving forces," J. Am. Chem. Soc. vol. 118, pp. 1961-1965 (1996).
Nikolenko et al., "Two-photon uncaging of Neurochemicals using inorganic metal complexes," Chem. Commun. pp. 1752-1754 (2005).
Pinnick et al., "Photosubstitution reactions of Ru(bpy)2XYn+ complexes," Inorg. Chem, vol. 23, pp. 1440-1445 (1984).
PubChem Iodeosin, http://pubchem.ncbi.nlm.nih.gov/summary/summary.cgi?sid=458734&loc=es_rss#synonyms, Release date Oct. 2011, printed on Feb. 6, 2013 (2 pages).
Salierno et al., "A fast ruthenium polypyridine cage complex photoreleases glutamate with visible or IR light in one and two photon regimes." J. Inorg. Biochem. vol. 104, No. 4, pp. 418-422 (2010).
Salierno et al., "Caged Amino Acids for Visible-Light Photodelivery," European Journal of Inorganic Chemistry vol. 2008, No. 7, pp. 1125-1128 (2008).
Saudek et al., "A Preliminary Trial of the Programmable Implantable Medication System for Insulin Delivery," The New England Journal of Medicine vol. 321, No. 9, pp. 574-579 (1989).
Schlue et al., "Extracellular Potassium in Neuropile and Nerve Cell Body Region of the Leech Central Nervous System," J. Exp. Biol. vol. 87, pp. 23-43 (1980).
Sefton, "Implantable Pumps," CRC Crit. Rev. Biomed. Eng. vol. 14, No. 3, pp. 201-240 (1987).
Smolen et al., "Controlled Drug Bioavailability: Volume 1 Drug Product Design and Performance," Wiley New York, 1984, table of contents (3 pages).
Strickler et al., "Three-dimensional optical data storage in refractive media two-photon point excitation," Optics Letters vol. 16, No. 22, pp. 1780-1782 (1991).
Treat et al., "Liposome Encapsulated Doxorubicin Preliminary Results of Phase I and Phase II Trials," Liposomes in the Therapy of Infectious Disease and Cancer, Alan R. Liss, Inc., NY, pp. 353-365 (1989).
Utzinger et al., "Fiber optic probes for biomedical optical spectroscopy," Journal of Biomedical Optics 8(1), 121-147 (2003).
Utzinger, Urs, et al., "Fiber optic probes for biomedical optical spectroscopy", J. Biomed. Optics, Jan. 2003, vol. 8, No. 1, pp. 121-147.
Viala, "An expeditious route to cis-Ru(bpy)2Cl2 (bpy=2,2'-bypyridine) using carbohydrates as reduces," Inorg. Chim. Acta vol. 359, pp. 984-989 (2006).
Wu et al., "Receptor-mediated in Vitro Gene Transformation by a Soluble DNA Carrier System," J. Biol. Chem vol. 262, No. 10, pp. 4429-4432 (1987).
Zayat et al., "A New Strategy for Neurochemical Photodelivery: Metal-Ligand Heterolytic Cleavage," J. Am. Chem. Soc. 125 pp. 882-883 (2003).
Zayat et al., "Ruthenium(II) Bipyridyl Complexes as Photolabile Caging Groups for Amines," Inorganic Chemistry vol. 45, No. 4, pp. 1728-1731 (2006).
Zoepf, "Photodynamic therapy of cholangiocarcinoma," HPB vol. 10, pp. 161-163 (2008).

\* cited by examiner (RS)-(Tetrazol-5-yl)glycine

PHOTOLABILE COMPOUNDS

CROSS-REFERENCE TO RELATED APPLICATION

This application is a continuation of U.S. application Ser. No. 13/279,876, filed Oct. 24, 2011, which is a divisional application of U.S. application Ser. No. 10/585,013, filed Oct. 19, 2007, which is the U.S. National Phase Entry under 35 U.S.C. §371 of International Patent Application No. PCT/US2004/042147, filed Dec. 14, 2004, which claims the benefit of and priority to U.S. Provisional Patent Application No. 60/532,976, filed Dec. 29, 2003, the disclosure of each of which is hereby incorporated by reference herein in its entirety.

This invention was made with government support under Grant Nos. EY011787 and EY013237 awarded by the National Institute of Health, and under Contract No. C000082 awarded by NYSTAR. The government has certain rights to the invention.

This patent disclosure contains material which is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

FIELD OF THE INVENTION

The present invention relates generally to novel Photolabile Compounds and methods for uncaging an organic molecule, such as a bioactive molecule, which can have a variety of uses both in vitro and in vivo.

BACKGROUND OF THE INVENTION

Photolabile protecting groups, which are also called caging groups, are classes of protecting groups that are particularly useful in the biological sciences. Because light can be controlled with precision both spatially and temporally, cleaving a protecting group from a bioactive molecule allows release, or uncaging, of the molecule. Protecting groups typically mask or conceal charged (for example, carboxylate or phosphate) or polar (for example, amine, hydroxyl, or sulfhydryl) groups on the compounds. Frequently such functionalities increase the hydrophobicity and membrane permeability of the protected molecules. Prior to photolysis, the Photolabile Compounds are typically chemically or biologically inactive because at least one of the compounds' main functionalities is blocked. The activity of the molecule can be triggered by a pulse of light, thereby releasing the molecule from the photoreleasable compound. Thus, photolabile protecting groups can be removed from a protected compound by irradiation, for example, to control the release of the compound when and where desired, either in vivo or in vitro.

Commercially available Photolabile Compounds typically require ultraviolet (UV) light to remove the compounds from the cage. However, UV light can cause damage to organs, tissues and cells, thus making UV light detrimental for in vivo use. Thus, there is a need in the art to utilize new Photolabile Compounds having ligands that can be released using light other than UV light, particularly for in vivo applications. The present invention provides novel Photolabile Compounds and methods for using the compounds, which provide advantages over currently available compounds that are photolabile using only UV light.

SUMMARY OF THE INVENTION

It is an aspect of the present invention to provide novel Photolabile Compounds that protect an organic molecule, such as a bioactive molecule. Upon exposure to light, the organic molecule is released, and is useful in the methods described herein.

Accordingly, the present invention provides compounds of Formula I:

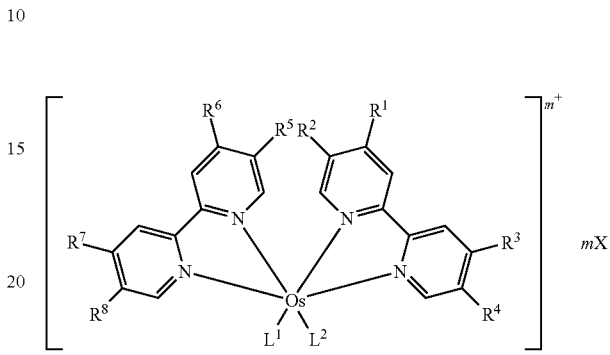

wherein:
each $L^1$ is independently an organic molecule having:
(a) a 5-membered monocyclic aromatic ring, one of the ring's members being a nitrogen atom that forms a bond with Os;
(b) a 6-membered monocyclic aromatic ring, one of the ring's members being a nitrogen atom that forms a bond with Os;
(c) an 8-10-membered bicyclic ring, one of the bicyclic rings being aromatic and having a nitrogen atom member that forms a bond with Os;
(d) an —$NH_2$ group whose nitrogen atom forms a bond with Os; or
(e) a —COOH group, one of whose oxygen atoms forms a bond with Os;
$L^2$ is $(R^2)_3P$, $(R^2O)_3P$, or $L^1$, wherein each $R^2$ is independently —$C_1$-$C_{18}$ alkyl, —$C_3$-$C_8$ cycloalkyl, or phenyl, and m is 2; or $L^2$ is —CN and m is 1;
$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and
X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In another aspect, the present invention provides compounds of Formula II:

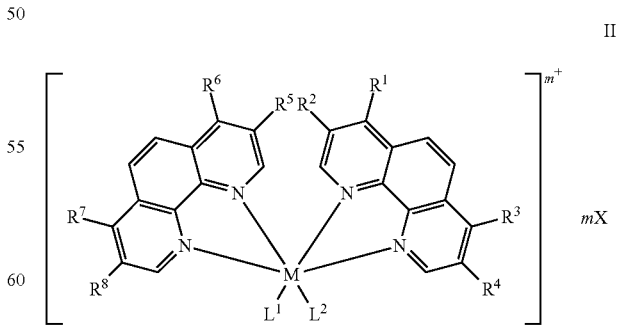

wherein M is Ru or Os;
each $L^1$ is independently an organic molecule having:
(a) a 5-membered monocyclic aromatic ring, one of the ring's members being a nitrogen atom that forms a bond with M;

(b) a 6-membered monocyclic aromatic ring, one of the ring's members being a nitrogen atom that forms a bond with M;

(c) an 8-10-membered bicyclic ring, one of the bicyclic rings being aromatic and having a nitrogen atom member that forms a bond with M;

(d) an —$NH_2$ group whose nitrogen atom forms a bond with M; or (e) a —COOH group, one of whose oxygen atoms forms a bond with M;

$L^2$ is $(R^2)_3P$, $(R^2O)_3P$, or $L^1$, wherein each $R^2$ is independently —$C_1$-$C_{18}$ alkyl, —$C_3$-$C_8$ cycloalkyl, or phenyl, and m is 2; or $L^2$ is —CN and m is 1;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In another aspect, the present invention provides compounds of Formula III:

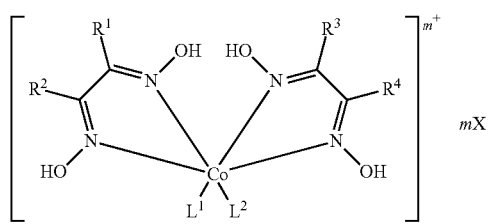

III wherein:

each $L^1$ is independently an organic molecule having:

(a) a 5-membered monocyclic aromatic ring, one of the ring's members being a nitrogen atom that forms a bond with Co;

(b) a 6-membered monocyclic aromatic ring, one of the ring's members being a nitrogen atom that forms a bond with Co;

(c) an 8-10-membered bicyclic ring, one of the bicyclic rings being aromatic and having a nitrogen atom member that forms a bond with Co;

(d) an —$NH_2$ group whose nitrogen atom forms a bond with Co; or (e) a —COOH group, one of whose oxygen atoms forms a bond with Co;

$L^2$ is $(R^2)_3P$, $(R^2O)_3P$, or $L^1$, wherein each $R^2$ is independently —$C_1$-$C_{18}$ alkyl, —$C_3$-$C_8$ cycloalkyl, or phenyl, and m is 3; or $L^2$ is —CN, —Cl, Br, —I or —$N_3$ and m is 2;

$R^1$ to $R^4$ are independently —$C_1$-$C_{18}$ alkyl; and

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In another aspect, the present invention provides compounds of Formula IVa:

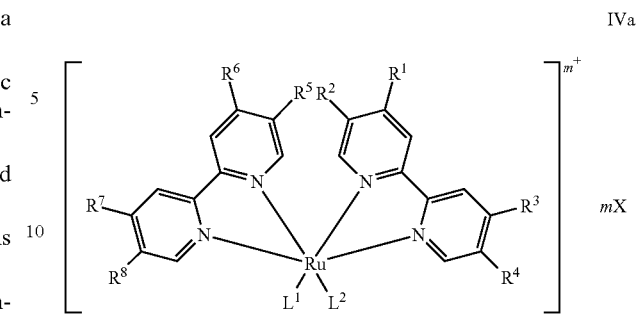

IVa wherein:

each $L^1$ is independently an organic molecule having:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru; or (e) a —COOH group, one of whose oxygen atoms forms a bond with Ru;

$L^2$ is $(R^2)_3P$, $(R^2O)_3P$, or $L^1$, wherein each $R^2$ is independently —$C_1$-$C_{18}$ alkyl, —$C_3$-$C_8$ cycloalkyl, or phenyl, and m is 2; or $L^2$ is —CN and m is 1.

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In another aspect, the present invention provides compounds of Formula IVb:

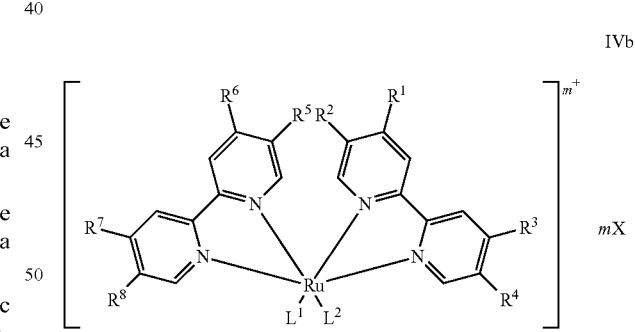

IVb wherein:

$L^1$ is 4-aminopyridine (4-AP), whose pyridyl nitrogen atom forms a bond with Ru;

$L^2$ is $(R^2)_3P$, $(R^2O)_3P$, or $L^1$, wherein each $R^2$ is independently —$C_1$-$C_{18}$ alkyl, —$C_3$-$C_8$ cycloalkyl, or phenyl, and m is 2; or $L^2$ is —CN and m is 1;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In another aspect, the present invention provides compounds of Formula V:

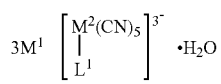

wherein:
M¹ is Li⁺, Na⁺, or K⁺;
M² is Fe, Ru, or Os;
and L¹ is independently an organic molecule having:
(a) a 5-membered monocyclic aromatic ring, one of the ring's members being a nitrogen atom that forms a bond with M²;
(b) a 6-membered monocyclic aromatic ring, one of the ring's members being a nitrogen atom that forms a bond with M²;
(c) an 8-10-membered bicyclic ring, one of the bicyclic rings being aromatic and having a nitrogen atom member that forms a bond with M²;
(d) an —NH₂ group whose nitrogen atom forms a bond with M²; or
(e) a —COOH group, one of whose oxygen atoms forms a bond with M².

A compound of Formula I-V ("a Photolabile Compound") releases L¹ upon exposure to light.

In another aspect, the present invention provides a composition comprising an effective amount of a Photolabile Compound and a physiologically acceptable carrier, vehicle, diluent, or excipient.

In another aspect, the present invention provides a vessel containing a Photolabile Compound.

In yet another of its aspects, the present invention provides a kit comprising a Photolabile Compound and instructions for use.

Another aspect of the present invention provides methods for releasing an organic molecule from a Photolabile Compound, comprising exposing a Photolabile Compound to light under conditions sufficient to release the organic molecule.

In yet another aspect, the present invention provides a method for protecting an organic molecule from an effect of an enzyme, comprising allowing the organic molecule and a compound of Formula I':

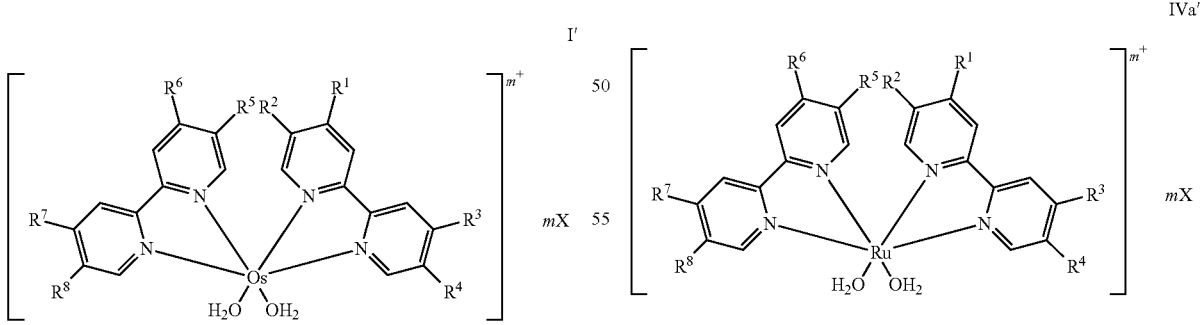

wherein m is 2; R¹-R⁸, the organic molecule, and X are as described for Formula I, to react under conditions sufficient to make a compound of Formula I.

In another aspect, the present invention provides methods for protecting an organic molecule from an effect of an enzyme, comprising allowing the organic molecule and a compound of Formula II':

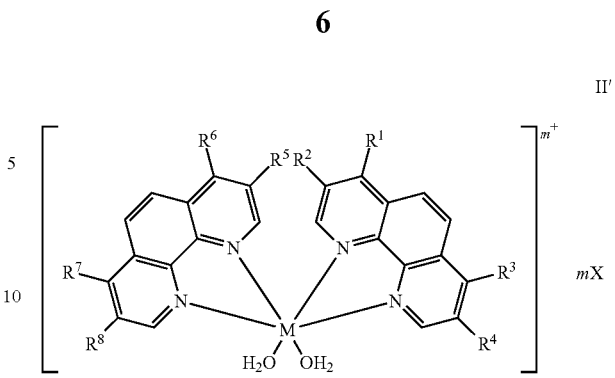

wherein m is 2; and R¹-R⁸, the organic molecule, and X are as described for Formula II, to react under conditions sufficient to make a compound of Formula II.

In another aspect, the present invention provides methods for protecting an organic molecule from an effect of an enzyme, comprising allowing the organic molecule and a compound of Formula III':

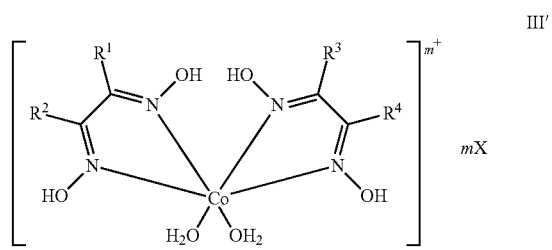

wherein m is 3; and R¹-R⁴, the organic molecule, and X are as described for Formula III, to react under conditions sufficient to make a compound of Formula III.

In another aspect, the present invention provides methods for protecting an organic molecule from an effect of an enzyme, comprising allowing the organic molecule and a compound of Formula IVa':

wherein m is 2; and R¹-R⁸, the organic molecule, and X are as described for Formula IVa, to react under conditions sufficient to make a compound of Formula IVa.

In another aspect, the present invention provides methods for protecting an organic molecule from an effect of an enzyme, comprising allowing the organic molecule and a compound of Formula IVb':

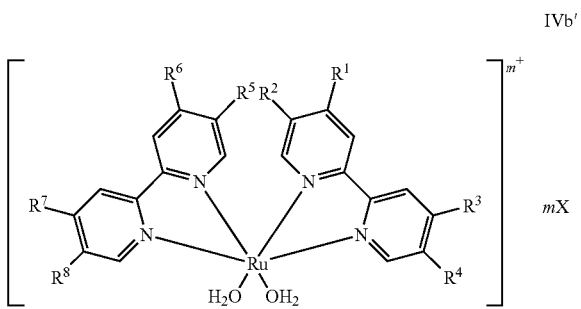

wherein m is 2; and $R^1$-$R^8$, the organic molecule, and X are as described for Formula IVb, to react under conditions sufficient to make a compound of Formula IVb.

In another aspect, the present invention provides methods for protecting an organic molecule from an effect of an enzyme, comprising allowing the organic molecule and a compound of Formula V':

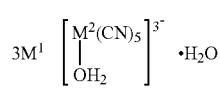

wherein $M^1$ and the organic molecule are as described for Formula V, to react under conditions sufficient to make a compound of Formula V.

In yet another aspect, the present invention provides a method for making an organic molecule bioavailable to a subject in need of the organic molecule, comprising administering a Photolabile Compound to the subject; and exposing the compound to light under conditions sufficient to release the organic molecule from the compound.

In another aspect, the present invention provides methods for assaying an organic molecule, comprising: (a) exposing a Photolabile Compound and a biological sample to light under conditions sufficient to release the organic molecule from the Photolabile Compound, and (b) determining an effect of the organic molecule on the biological sample.

Additional aspects, features and advantages afforded by the present invention will be apparent from the detailed description, figures, and exemplification hereinbelow.

BRIEF DESCRIPTION OF THE FIGURES

FIG. 7A shows a recording of Retzius neuron voltage activity during perfusion of free 4AP on the leech ganglia. [4AP]=0, 10, 20 and 50 mM. Flow rate=1 ml/min. Carrier: saline solution, as described in Example 3. FIG. 7B shows the recording of Retzius neuron activity during exposure to a 0.1 msec flash of green light through the filter of FIG. 6. Flow rate=1 ml/min. Carrier: saline solution, as described in Example 3. Pulse energy: 0.5 J.

FIG. 8A: spectrum changes of [Ru(bpy)$_2$(4AP)$_2$]Cl$_2$ during irradiation with 473 nm laser light. Power: 6.39 mW continuous. Initial concentration of [Ru(bpy)$_2$(4AP)$_2$]Cl$_2$: 27.9 μM. A(473 nm)=0.18. FIG. 8B: Fraction of [Ru(bpy)$_2$(4AP)(H$_2$O)]$^{2+}$ as a function of irradiation time obtained from the spectra depicted in FIG. 8A.

FIG. 13A depicts the structure of TzGly. FIG. 13B demonstrates the spiking of a mouse cortical neuron caused by the addition of TzGly (1 μM) to neuron via perfusion. The measurement results were obtained by the whole-cell patch-clamp method, as known and used in the art.

FIGS. 14A, B and C show fluorescent-image micrographs of a neuron, including magnified views of dendritic spines. FIG. 14D shows the effect of laser irradiation (~40 mW) on the spiking of a single neuron in the presence of [Ru(bpy)$_2$(TzGly)$_2$]Cl$_2$. Concentration of [Ru(bpy)$_2$(TzGly)$_2$]Cl$_2$=100 μM; Pulse length: 10 ms; Power: 40 mW; Wavelength: 720 nm. FIGS. 14E-G relate to experiments carried out as controls to the experiments of FIGS. 14A-D. FIGS. 14E and F show magnified views of the dendritic spines of a neuron. FIG. 14G presents a plot showing the effect of laser irradiation on a control neuron in the absence of [Ru(bpy)$_2$(TzGly)$_2$]Cl$_2$. No increased activity is observed. Pulse length: 10 ms; Power: 40 mW; Wavelength: 720 nm.

DETAILED DESCRIPTION OF THE INVENTION

Figure 1:
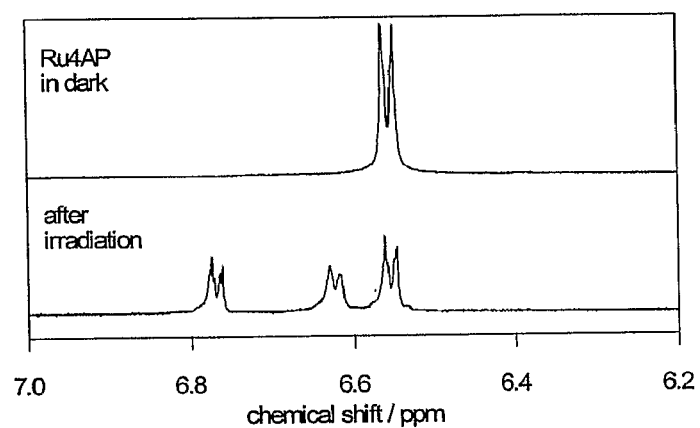
FIG. 1 depicts a partial $^1$H NMR spectra of [Ru(bpy)$_2$(4AP)$_2$]Cl$_2$, as described herein (Example 1), showing the signals corresponding to the 4-AP meta hydrogens. m1: in [Ru(bpy)$_2$(4AP)$_2$]$^{2+}$; m2: in [Ru(bpy)$_2$(H$_2$O)(4AP)$_2$]$^{2+}$; m3: in free ligand 4-AP.

The present invention relates generally to Photolabile Compounds comprising organic molecules and methods for using the Photolabile Compounds. The organic molecules can be biologically active. In one embodiment of this invention, an organic molecule, e.g., a biologically active molecule, is protected and subsequently released upon exposure to light, advantageously, visible light.

In contrast to known methods, visible light, e.g., a visible light pulse, can be used to release an organic molecule from a Photolabile Compound. Thus, in the present methods, samples, e.g., organs, tissues or cells, or subjects to which a Photolabile Compound is administered, undergo only minimal, if any, exposure to UV radiation, which has detrimental effects on cellular components and, ultimately, on cell growth and viability.

In accordance with the present invention, and without wishing to be bound by theory, the metal (M)-organic molecule bond is normally weaker than a covalent a bond, and therefore can be broken using a lower energy irradiation. Further in accordance with this invention, and without wishing to be bound by theory, the energy required for the release of an organic molecule by exposure to light is relatively low. In the Photolabile Compounds of this invention, the organic molecule is photoreleased by irradiation of the Photolabile Compound using light as described herein.

Also, according to this invention, photorelease can occur in vivo or in a biological sample, e.g., a body fluid, a body sample, such as an organ or tissue sample, in living cells and in the body. Thus, the Photolabile Compounds are especially valuable for in vivo biological applications, such as treatments for various diseases, conditions and disorders of the body. The use of Photolabile Compounds as described herein allows precise control of the onset of a bioactive function or a bioactivity in the body, for example, in living organs, tissues, and cells, i.e., within microseconds to milliseconds, with minimal harm to a biological sample, or to the body or its organ, tissue and cellular components. In addition, exposure of a biological sample to light can be localized to the site where an organic molecule is needed or desired. This is particularly beneficial for administration to a subject, particularly a human patient.

The Photolabile Compounds are also suitable for use in non-biological systems, such as in solar cells, photocells, or an optical memory, e.g., a three dimensional optical memory.

In one embodiment, the invention encompasses compounds of Formula I:

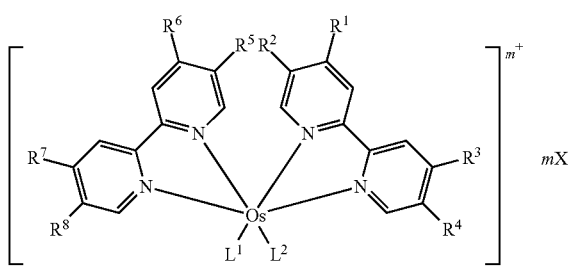

wherein:

$R^1$-$R^8$, $L^1$, $L^2$, X and m are as defined above for the compounds of Formula I.

In another embodiment, the invention encompasses a compound of Formula II:

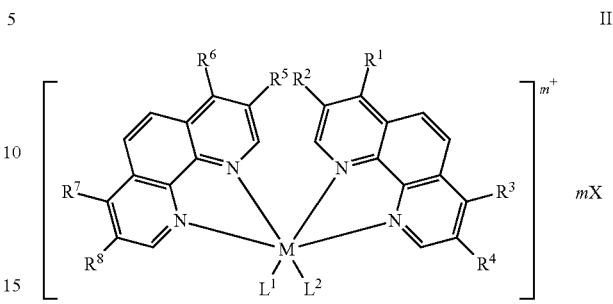

wherein:

$R^1$-$R^8$, $L^1$, $L^2$, X, M and m are as defined above for the compounds of Formula II.

In another embodiment, the invention encompasses a compound of Formula III:

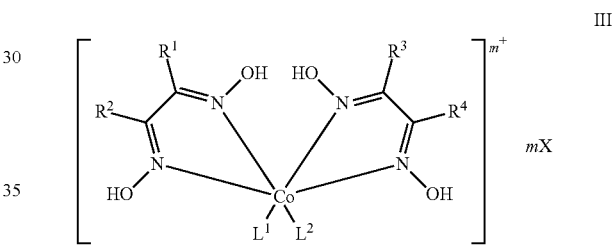

wherein:

$R^1$-$R^4$, $L^1$, $L^2$, X and m are as defined above for the compounds of Formula III.

In another embodiment, the invention encompasses a compound of Formula IVa:

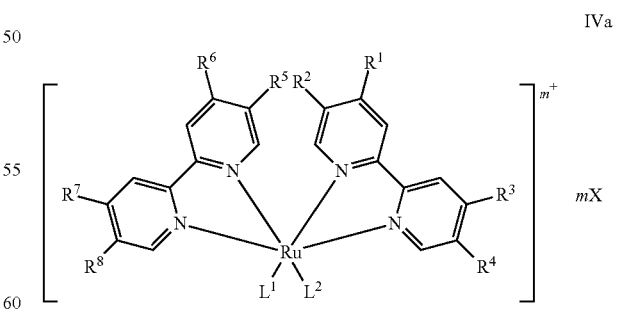

wherein:

$R^1$-$R^8$, $L^1$, $L^2$, X and m are as defined above for the compounds of Formula IVa.

In another embodiment, the invention encompasses a compound of Formula IVb:

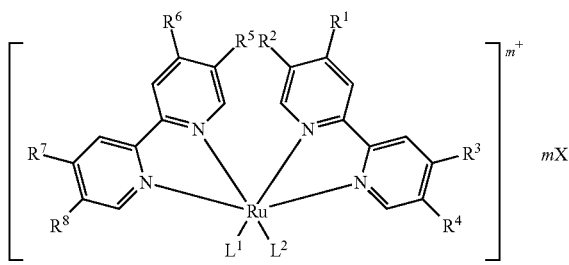

wherein:

$R^1$-$R^8$, $L^1$, $L^2$, X and m are as defined above for the compounds of Formula IVb.

In another embodiment, the invention encompasses a compound of Formula V:

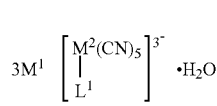

wherein $M^1$, $M^2$, and $L^1$ are as defined above for the compounds of Formula V.

The Photolabile Compounds of Formulas I, II, IVa, IVb and V can exists in a cis or trans configuration. Accordingly, Formulas I, II, IVa, IVb and V encompass both cis and trans forms of the Photolabile Compounds.

It is to be understood the Photolabile Compounds of Formula III exist only in a trans configuration.

In the compounds of Formulae I-IVb, —($C_1$-$C_{18}$) alkyl refers to a saturated straight or branched non-cyclic hydrocarbon having 1 to 18 carbon atoms. Representative saturated straight chain —($C_1$-$C_{18}$) alkyls include -methyl, -ethyl, -n-propyl, -n-butyl, -n-pentyl, -n-hexyl, -n-heptyl, -n-octyl, -n-nonyl, -n-decyl, -n-undecyl, -n-dodecyl, -n-tridecyl, -n-tetradecyl, - n-pentadecyl, -n-hexadecyl, -n-heptadecyl and -n-octadecyl. Representative saturated branched —($C_1$-$C_{18}$) alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,2-dimethylhexyl, -2,3-dimethylhexyl, -2,4-dimethylhexyl, -2,5-dimethylhexyl, -2,2-dimethylpentyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl-2-ethylpentyl, -2-methyl-3-ethylpentyl, -2-methyl-4-ethylpentyl, -2-methyl-2-ethylhexyl, -2-methyl-3-ethylhexyl, -2-methyl-4-ethylhexyl, -2,2-diethylpentyl, -3,3-diethylhexyl, -2,2-diethylhexyl, -3,3-diethylhexyl and the like.

In the compounds of the present invention, —($C_3$-$C_8$) cycloalkyl refers to a saturated cyclic hydrocarbon having from 3 to 8 carbon atoms. Representative —($C_3$-$C_8$) cycloalkyls include -cyclopropyl, -cyclobutyl, -cyclopentyl, -cyclohexyl, -cycloheptyl and -cyclooctyl hydrocarbons.

An amino acid group, such as an α-amino acid, is an organic molecule having an amino group (—$NH_2$) and a carboxylic acid group. An amino acid can be one of the 20 common α-amino acids (Gly, Ala, Val, Leu, Ile, Ser, Thr, Asp, Asn, Lys, Glu, Gln, Arg, His, Phe, Cys, Trp, Tyr, Met and Pro), or another naturally occurring amino acid, such as norleucine, ethylglycine, ornithine, gamma-amino butyric acid, and phenylglycine.

Examples of a 6-membered monocyclic aromatic ring, wherein one of the ring's members is a nitrogen atom, include a pyridyl, pyrimidinyl, pyridazinyl and pyrazinyl ring.

Examples of a 5-membered monocyclic aromatic ring, wherein one of the ring's members is a nitrogen atom, include a pyrrolyl, imidazolyl, pyrazolyl, triazolyl, tetrazolyl, oxazolyl, oxadiazolyl, thiazolyl and thiadiazolyl ring.

Examples of an 8-10-membered bicyclic aromatic ring, wherein one of the rings is aromatic and has a nitrogen atom member, include an indolizinyl, isoindolyl, 3H-indolyl, indolyl, indazolyl, purinyl, quinolyl, isoquinolyl, phthalazinyl, naphthyridinyl, quinoxalinyl, 1,3,7-trimethyl-2,6-dioxopurinyl, quinazolinyl, cinnolinyl, pteridinyl, 6-amino-1H-purinyl and 2-aminohypoxanthinyl bicyclic aromatic ring.

In general terms, illustrative examples of organic molecules useful in the present Photolabile Compounds embrace a variety of agents, such as pharmaceutical agents, small molecules, drugs, neurochemicals, peptides, proteins, and chemotherapeutic agents, as nonlimiting examples.

Illustrative organic molecules can further include luciferin, enzyme inhibitors, fatty acids (e.g., arachidonic acid), protein kinase C activators (e.g., dioctanoylglycerol), tubulin assembly promoters (e.g., paclitaxel), antibiotics (e.g., penicillins or A23187), neurotransmitters (e.g., L-glutamic acid, aspartic acid, carbamylcholine, dopamine, epinephrine, GABA, glutamic acid, glycine, haloperidol, isoproterenol, kainic acid, NMDA, NMDA receptor antagonist MK-801, norepinephrine, phenylephrine, propranolol), 4-aminopyridine (4AP), serotonin (5 hydroxytryptamine, 5HT), (RS)-(tetrazol-5-yl) glycine (TzGly), tetrazolyl-α-amino-3-hydroxy-5-methyl-4-isoxazoleproprionic acid ((tetrazol-5-yl) AMPA), nicotine, nicotinic acid, isoxazole, and fluorescent dyes (e.g., fluorescein, HPTS, rhodamines, succinimidyl esters and sulfosuccinimidyl esters of carboxy-Q-rhodamine, or Rhodamine Green), nucleotides (e.g., ATP, ADP, cAMP, GDP, GTP, cGMP, GTP-γ-S, GDP-β, 8-substituted derivatives of cAMP or cGMP, e.g., 8-bromo-cAMP, 8-bromo-cGMP, 8-chloro-cAMP, 8-chloro-cGMP, 8-parachlorophenylthio (cCPT) cAMP or cGMP, phosphates (e.g., phosphates, phosphate esters), phenylphosphate ($PPh_3$), Py, nucleosides, nucleoside derivatives, nucleotide derivatives (e.g., cADP-ribose, 8-amino-cADP ribose, or 8-bromo-cADP-ribose), cyclitols (e.g., inositol), cyclitol phosphates (e.g., myo-inositol phosphate, myo-inositol-1,4,5-triphosphate, myo-inositol-1,3,4,5-tetrakisphosphate, or myo-inositol-3,4,5,6-tetrykisphosphate), NO (e.g., from the decomposable compound HON=N(O) ($Net_2$)), chelants (e.g., EDTA, EGTA), and ionophores (e.g., nigericin). The organic molecule can be cell permeant, as described, for example, in Furuta et al., *Biochem. Biophys. Res. Commun.*, 228:193-198 (1996).

Especially useful examples of organic molecules include adenosine 5'-diphosphate ADP; adenosine 5'-triphosphate ATP; adenosine 5'-monophosphate AMP; aminobutyric acid; L-glutamic acid; cyclic adenosine 5'-diphosphate ribose; adenosine 3', 5'-cyclicmonophosphate; fluorescein; methyl-D-aspartic acid; tyramine; tryptophan; 4-aminopyridine (4AP); epinephrine; norepinephrine; dopamine; serotonin (5 hydroxytryptamine, 5HT); (RS)-(tetrazol-5-yl) glycine (TzGly), which is a potent N-methyl-D-aspartate receptor (NMDA) agonist; tetrazolyl-α-amino-3-hydroxy-5-methyl-4-isoxazolepropionic acid ((tetrazol-5-yl) AMPA); caffeine and nicotine.

In accordance with this invention, the organic molecule ligands glutamate, gamma aminobutyric acid (GABA), alaninate, glycinate and the like have been demonstrated to photorelease from a Photolabile Compound after exposure to visible light; such Photolabile Compounds are stable in solutions in addition to water. Organic molecules having an —$NH_2$ group or an —COOH group are preferably released in solvents other than water, for example, alcohol (e.g., methanol, ethanol), acetone, etc.

The Photolabile Compounds of Formulas I, II, IVa and IVb where $L_2$ is other than $L_1$ can be made by allowing about a molar equivalent of $M(bdt)_2Cl_2$, where M is Os or Ru and bdt is bipyridine or phenanthroline substituted with an $R_1$-$R_8$ group as defined in Formula I, II, IVa or IVb, to react with about a molar equivalent of an organic molecule in water, ethanol, methanol, isopropyl alcohol, ethylene glycol, acetone, methylene chloride or a mixture thereof at reflux under nitrogen. After about 4 to about 8 hours, the resultant solution is cooled and to it is added at least about an equivalent of $L_2$. The resultant mixture is heated at reflux for about 4 to about 20 h. After cooling to room temperature, the resultant solution is diluted with water, and to it is added excess $NH_4PF_6$. The resultant precipitate is filtered, purified via silica-gel chromatography, dried and dissolved in acetone. (n-Bu)$_4$NH$_4^+$X, wherein X is defined in Formula I, II, IVa or IVb, is added to the acetone solution, and the resultant Photolabile Compound of Formula I, II, IVa or IVb where $L_2$ is other than $L_1$ is filtered.

The Photolabile Compounds of Formulas I, II, IVa and IVb where $L_2$ is $L_1$ can be made by allowing about a molar equivalent of $M(bdt)_2Cl_2$, where M is Os or Ru and bdt is bipyridine or phenanthroline substituted with an $R_1$-$R_8$ group as defined in Formula I, II, IVa or IVb, to react with an excess amount of an organic molecule in water, ethanol, methanol, isopropyl alcohol, ethylene glycol, acetone, methylene chloride or a mixture thereof at reflux under nitrogen. After about 4 to about 8 hours, the resultant solution is cooled to room temperature. The resultant mixture is diluted with water, and to it is added excess $NH_4PF_6$. The resultant precipitate is filtered, purified via silica-gel chromatography, dried and dissolved in acetone. (n-Bu)$_4$NH$_4^+$X, wherein X is defined in I, II, IVa or IVb, is added to the acetone solution, and the resultant Photolabile Compound of Formula I, II, IVa or IVb where $L_2$ is $L_1$ is filtered.

The Photolabile Compounds of Formula III can be made by adding about 2 equivalents of a di($C_1$-$C_{18}$ alkyl)glyoxime to $CoY_2$, wherein Y is OAc, $NO_3$ or Cl, in 1:1 ethanol:water with stirring, wherein the concentration of $CoY_2$ in 1:1 ethanol:water ranges from about 10 to about 100 mg/mL. To the resultant mixture is added about 1 equivalent of an organic molecule and about 1 equivalent of $L_2$ where $L_1$ is other than $L_2$, or at least about 2 equivalents of the organic molecule where $L_2$ is $L_1$. $O_2$ is then is bubbled into the solution, resulting in a precipitation of the Photolabile Compounds of Formula III.

The Photolabile Compounds of Formula V where $M^2$ is Fe or Ru can be obtained by dissolving about 1 molar equivalent of $(M^1)_3[M^2(CN)_5NH_3]2H_2O$, where $M^1$ is defined in Formula V, in about 15 mL of argon-deoxygenated 1:1 ethanol:water containing about 10 molar equivalents of the organic molecule. The resultant mixture is maintained at about room temperature under argon for about 1 hour and concentrated in vacuo at about room temperature to a volume of about 1 mL. To the resultant concentrate is added a cold, saturated ethanol solution of $M^1I$, resulting in a precipitation of the Photolabile Compounds of Formula V where $M^2$ is Fe or Ru, which are washed with ethanol and diethyl ether.

The Photolabile Compounds of Formula V where $M^2$ is Os can be obtained by dissolving about 1 molar equivalent of $(M^1)_3[Os(CN)_5NH_3]2H_2O$, where $M^1$ is defined in Formula V, in about 15 mL of argon-deoxygenated 1:1 ethanol:water containing about 10 molar equivalents of the organic molecule. The resultant mixture is maintained at about 80-90° C. under argon for about 3 h and concentrated in vacuo at about room temperature to a volume of about 1 mL. The resultant concentrate is purified via chromatography using Sephadex-25 (length, 1.5 m; diameter, 2.5 cm). Fractions containing $(M^1)_3[Os(CN)_5L^1]^{3-}$ are collected and concentrated at about room temperature in vacuo. To the resultant residue is added a cold, saturated ethanol solution of $M^1I$, resulting in a precipitation of the Photolabile Compounds of Formula V where $M^2$ is Os, which are washed with ethanol and diethyl ether.

For the present invention, photorelease can generally occur rapidly, e.g., after about 1 microsecond to about 500 or milliseconds following exposure to visible light of the appropriate wavelength. Suitable wavelengths of light for effective photorelease of an organic molecule from a Photolabile Compound range from about 300 to about 500 nm, or from about 300 to about 360 nm, or from about 450 to about 500 nm, e.g., 473 nm. Suitable light sources include those which are capable of irradiating light of the appropriate wavelengths, for example and without limitation, commercially available tungsten lamps (Cole-Parmer), arc lamps, xenon continuous lamps, lasers, e.g., blue lasers or photooptic light sources. Such light sources are commercially available (CrystaLaser, Reno, Nev.; Lasever, Jiangdong, Ningbo, China). Other forms of light, such as sunlight, infrared light, pulsed infrared light, or UV radiation can also be used for the invention, as necessary or desired.

Devices and systems suitable for exposing the Photolabile Compounds to light, particularly visible or infrared light, further include imaging probes, imaging catheters and fiber optic probes, particularly those containing gradient index, or graded-index, (GRIN) lenses, which are described in U. Utzinger et al., 2003, *J. Biomed. Optics*, 8(1):121-147; and Fujimoto et al., *Photonic Materials, Devices and Systems—Laser Medicine and Medical Imaging Group*, RLE Progress Report 144, pp 27-1 to 27-35, and which are commercially available. (Sp3 plus, UK). The light suitable for exposing the Photolabile Compounds to photorelease an organic molecule comprises a wavelength of about 300 to about 500 nm, or about 300 to about 360 nm, or about 450 to about 500 nm. Preferred are visible or infrared light.

Further in accordance with this invention, the organic molecules can also be released from the Photolabile Compounds via one-photon or two-photon photolysis. Optical memories that utilize a two-photon excitation are described, for example, by Strickler and Webb, 1991, *Optics Letters*, 16:1780-1782. A feature of two-photon excitation is the elimination of out-of-focus background. (See, e.g., W. Denk et al., 1990, *Science*, 248:73-76). Thus, two-photon uncaging can release an organic molecule only in the plane of focus. (See, e.g., W. Denk et al., 1994, *Proc. Natl. Acad. Sci. USA*, 91:6629-6633).

In an embodiment, the present invention encompasses a compound of Formula I, wherein the organic molecule 4-AP. In another embodiment, the invention encompasses a compound of Formula I, wherein the organic molecule is TzGly. In another embodiment, the invention encompasses a compound of Formula I, wherein the organic molecule is (tetrazol-5-yl) AMPA. In another embodiment, the invention encompasses a compound of Formula I, wherein the organic molecule is nicotine or caffeine. In another embodiment, the invention encompasses a compound of Formula I, wherein the organic molecule is serotonin, epinephrine, norepinephrine, or dopamine. In another embodiment, the present invention encompasses a compound of Formula I, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3', 5'-cyclicmonophosphate. In another embodiment, the invention encompasses a compound of Formula I wherein the organic molecule is aminobutyric acid or L-glutamic acid, or methyl-D-aspartic acid.

In an embodiment, the present invention encompasses a compound of Formula II, wherein the organic molecule is 4-AP. In another embodiment, the invention encompasses a compound of Formula II, wherein the organic molecule is TzGly. In another embodiment, the invention encompasses a compound of Formula II, wherein the organic molecule is (tetrazol-5-yl) AMPA. In another embodiment, the invention encompasses a compound of Formula II, wherein the organic molecule is nicotine or caffeine. In another embodiment, the invention encompasses a compound of Formula II, wherein the organic molecule is serotonin, epinephrine, norepinephrine, or dopamine. In another embodiment, the present invention encompasses a compound of Formula II, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3', 5'-cyclicmonophosphate. In another embodiment, the invention encompasses a compound of Formula II wherein the organic molecule is aminobutyric acid or L-glutamic acid, or methyl-D-aspartic acid.

In an embodiment, the present invention encompasses a compound of Formula III, wherein the organic molecule is 4-AP. In another embodiment, the invention encompasses a compound of Formula III, wherein the organic molecule is TzGly. In another embodiment, the invention encompasses a compound of Formula III, wherein the organic molecule is (tetrazol-5-yl) AMPA. In another embodiment, the invention encompasses a compound of Formula III, wherein the organic molecule is nicotine or caffeine. In another embodiment, the invention encompasses a compound of Formula III, wherein the organic molecule is serotonin, epinephrine, norepinephrine, or dopamine. In another embodiment, the present invention encompasses a compound of Formula III, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3', 5'-cyclicmonophosphate. In another embodiment, the invention encompasses a compound of Formula III wherein the organic molecule is aminobutyric acid or L-glutamic acid, or methyl-D-aspartic acid.

In an embodiment, the present invention encompasses a compound of Formula IVa or IVb, wherein the organic molecule is 4-AP. In another embodiment, the invention encompasses a compound of Formula IVa, wherein the organic molecule is TzGly. In another embodiment, the invention encompasses a compound of Formula IVa, wherein the organic molecule is (tetrazol-5-yl) AMPA. In another embodiment, the invention encompasses a compound of Formula IVa, wherein the organic molecule is nicotine or caffeine. In another embodiment, the invention encompasses a compound of Formula IVa, wherein the organic molecule is serotonin, epinephrine, norepinephrine, or dopamine. In another embodiment, the present invention encompasses a compound of Formula IVa, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3', 5'-cyclicmonophosphate. In another embodiment, the invention encompasses a compound of Formula IVa, wherein the organic molecule is aminobutyric acid or L-glutamic acid, or methyl-D-aspartic acid.

In an embodiment, the present invention encompasses a compound of Formula V, wherein the organic molecule is 4-AP. In another embodiment, the invention encompasses a compound of Formula V, wherein the organic molecule TzGly. In another embodiment, the invention encompasses a compound of Formula V, wherein the organic molecule is (tetrazol-5-yl) AMPA. In another embodiment, the invention encompasses a compound of Formula V, wherein the organic molecule is nicotine or caffeine. In another embodiment, the invention encompasses a compound of Formula V, wherein the organic molecule is serotonin, epinephrine, norepinephrine, or dopamine. In another embodiment, the present invention encompasses a compound of Formula V, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3', 5'-cyclicmonophosphate. In another embodiment, the invention encompasses a compound of Formula V, wherein the organic molecule is aminobutyric acid or L-glutamic acid, or methyl-D-aspartic acid.

In an embodiment, the present invention encompasses a composition comprising an effective amount of a Photolabile Compound and a physiologically acceptable carrier, vehicle, diluent, or excipient. Suitable carriers, vehicles, diluents, or excipients are known to those skilled in the art and include, without limitation, physiologically sterile saline and others as described herein.

In another embodiment, the composition comprises two or more Photolabile Compounds, each having a different metal, M.

In another embodiment, the present invention provides a vessel containing a Photolabile Compound. The vessel can further contain a biological sample, wherein the sample is, for example, hair, an organ specimen; a tissue or cell, for example, a neuronal tissue or cell; a tumor or cancer or neoplastic tissue or cell; or a tissue or cell removed from a patient or subject of interest. Tissue specimens sliced from microtomes, for example, are examples of suitable biological samples.

Any type of vessel that is capable of transmitting the wavelengths of light used for releasing the organic molecules comprising the Photolabile Compounds, and that is inert to solvent in which a Photolabile Compound is suspended, is suitable for use. For example, the vessel can be made of glass, plastic, acrylic, quartz, a noble metal, etc. In addition, if the vessel is composed of, or encased in, metal, e.g., aluminum, titanium, or stainless steel, exposure to light is performed through the top of the vessel, or through a "window" or other light-penetrable opening in the vessel. For solid-like materials, acrylic plastic or acrylamide-bisacrylamide gel, etc., for example, can be used as media in which the Photolabile Compounds are contained. For example, an acrylic plastic coating formulated using a $CHCl_3$ solution of acrylic and a Ru(bpy) complex changed its spectrum following irradiation, thus allowing photorelease in a solid state. For such solid state aspects of the invention, the temperature may be kept at 4K.

Solvents suitable in which a Photolabile Compounds can be exposed to light include aqueous solvents; water; acetonitrile; alcohol, e.g., methanol, ethanol; acetone; chlorinated solvents such as $CH_2Cl_2$ and $CHCl_3$; or dimethylsulfoxide.

Suitable temperatures at which a Photolabile Compound is exposed to light range, in general, from about 0° C. to about 100-150° C.

In another embodiment, this invention encompasses a method for releasing an organic molecule from a Photolabile Compound. The method comprises exposing a Photolabile Compound to light under conditions sufficient to release the organic molecule from the compound. In the method, the light comprises a wavelength of about 300 to about 500 nm, or about 300 to about 360 nm, or about 450 to about 500 nm. Further, the exposing can occur at a temperature from about 0° C. to about 150° C. In an embodiment, the methods of the invention comprise a Photolabile Compound, e.g., a compound of Formula I-IVb, light of a wavelength of about 300 nm to about 500 nm; $L^1$ being $L^2$, and a temperature of about 0° C. to about 150° C. In another embodiment, the methods comprise a Photolabile Compound, light of a wavelength of about 300 nm to about 360 nm; $L^1$ being $L^2$, and a temperature of about 0° C. to about 150° C. In another embodiment, the methods comprise a Photolabile Compound, light of a wavelength of about 450 nm to about 500 nm; $L^1$ being $L^2$, and a temperature of about 0° C. to about 150° C. In another embodiment, the methods comprise a Photolabile Compound, visible or infrared light; $L^1$ being $L^2$, and a temperature of about 0° C. to about 150° C. In another embodiment, the methods comprise a Photolabile Compound of Formula V, light of a wavelength of about 300 nm to about 500 nm and a temperature of about 0° C. to about 150° C. In another embodiment, the methods comprise a compound of Formula V, light of a wavelength of about 300 nm to about 360 nm and a temperature of about 0° C. to about 150° C. In another embodiment, the methods comprise a compound of Formula V, light of a wavelength of about 450 nm to about 500 nm and a temperature of about 0° C. to about 150° C. In another embodiment, the methods comprise a compound of Formula V, visible or infrared light and a temperature of about 0° C. to about 150° C.

In another embodiment, the present invention embraces a method of protecting an organic molecule from an effect of an enzyme, comprising allowing the organic molecule and a compound of Formula I':

I'

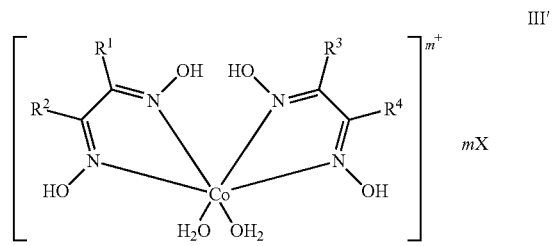

wherein m is 2, and $R^1$-$R^8$, the organic molecule, and X are as described for Formula I, to react under conditions sufficient to make a compound of Formula I.

Protection from an enzyme means that an organic molecule is concealed or masked from being acted upon by an enzyme, e.g., cleaved or modified, by an enzyme, prior to exposure of the Photolabile Compound to light.

In another embodiment, the present invention embraces a method of protecting an organic molecule from an effect of an enzyme, comprising allowing the organic molecule and a compound of Formula II':

II'

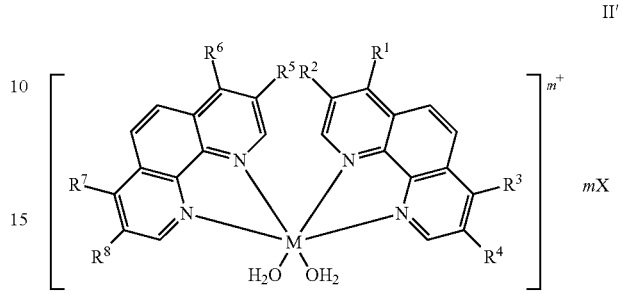

wherein m is 2, and $R^1$-$R^8$, the organic molecule, and X are as described for Formula II, to react under conditions sufficient to make a compound of Formula II.

In another embodiment, the present invention embraces a method of protecting an organic molecule from an effect of an enzyme, comprising allowing the organic molecule and a compound of Formula III':

III' wherein m is 3, and $R^1$-$R^4$, the organic molecule, and X as are described for Formula III, to react under conditions sufficient to make a compound of Formula III.

In another embodiment, the present invention embraces a method of protecting an organic molecule from an effect of an enzyme, comprising allowing the organic molecule and a compound of Formula IVa':

IVa' wherein m is 2 and $R^1$-$R^8$, the organic molecule, and X are as described for Formula IVa, to react under conditions sufficient to make a compound of Formula IVa.

In another embodiment, the present invention embraces a method of protecting an organic molecule from an effect of an enzyme, comprising allowing the organic molecule and a compound of Formula IVb':

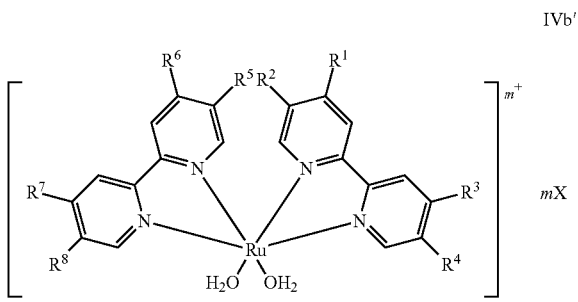

IVb' wherein m is 2 and $R^1$-$R^8$, the organic molecule, and X are as described for Formula IVb, to react under conditions sufficient to make a compound of Formula IVb.

In yet another embodiment, the present invention embraces a method of protecting an organic molecule from an effect of an enzyme, comprising allowing the organic molecule and a compound of Formula V':

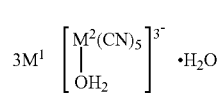

V' wherein $M^1$ is $Li^+$, $Na^+$, or $K^+$; and $M^2$ is Fe, Ru, or Os, to react under conditions sufficient to make a compound of Formula V.

In an embodiment, the invention encompasses a method for assaying an organic molecule, comprising exposing a Photolabile Compound and a biological sample to light under conditions sufficient to release the organic molecule from the Photolabile Compound, and (b) determining an effect of the organic molecule on the biological sample. The sample can be a biological sample, such as a sample excised, removed, or otherwise taken from a subject's body. The subject's biological sample can be, for example, a hair sample, an organ or tissue sample, e.g., from a biopsy or an autopsy, or a cell sample. In addition, the biological sample can be a body fluid sample. Body fluid samples include, without limitation, blood, serum, plasma, lymph, saliva, sputum, tears, semen, or urine. Biological samples can further include, without limitation, brain tissue, brain cells, muscle tissue, muscle cells, muscle fibers, fibroblasts, tissue slices, or fine tissue specimens, from any organ of the body, sarcoplasmic reticulum, skin tissue, membrane preparations or fragments, etc.

The light for exposing the compounds according to the methods of this invention can be sunlight, photo-optic light, or laser light. Advantageously, in the methods of this invention, the light for exposing the compound is other than UV radiation. Thus, for example, the light can be visible light or infrared light, including one-photon and two-photon light. The light can be emitted from a variety of sources, including without limitation, a laser light source, a tungsten light source, a photooptic light source, etc. Another advantage of visible light to expose or irradiate the compounds of the invention relates to the convenience and ability to use a visible light microscope, for example, to view a sample into which a compound is introduced and to microscopically visualize or monitor a photoreleased ligand from the compound after exposure to visible light. Because many microscopes do not transmit UV light, it is advantageous to be able to use a non-quartz microscope in accordance with this invention. Yet another advantage to the use of visible light is that it is not detrimental to living cells and tissues, making it beneficial for in vivo patient use. In addition, for patient use, the light can be specifically directed to an area where a Photolabile Compound is introduced or administered by the use of laser technology, fibers, probes, tubes, and the like. Such probes, fibers, or tubes can be directly inserted, for example, into a body cavity or opening, or under or through the skin, to expose the Photolabile Compound to light.

In another of its embodiments, the present invention embraces a method of making an organic molecule bioavailable to a subject. The organic molecule can be made bioavailable to a localized body region or area of the subject, or systemically to the whole body. Local bioavailability of the Photolabile Compounds is achieved, for example, via delivery devices and methods that allow the compounds to be directly administered, for example, inserted into a body cavity, or opening, or through or into the skin. The method of this embodiment involves administering a Photolabile Compound to the subject, and exposing the compound to light under conditions sufficient to release the organic molecule from the compound, thereby making the organic molecule bioavailable to the subject, and/or to a body site or region of the subject. The exposure to light can comprise the use of probes, fibers, tubes, and the like, which allow the light to be specifically directed to the area of interest on or within the body. Alternatively, the Photolabile Compounds can be administered to the patient kept in the dark; for photorelease of the organic molecule, the patient can be moved to the light where exposure to light and photorelease occur. In an embodiment according to this method, the organic molecule has:

(a) a 5-membered monocyclic aromatic ring, one of the ring's members being a nitrogen atom that forms a bond with a metal, M;

(b) a 6-membered monocyclic aromatic ring, one of the ring's members being a nitrogen atom that forms a bond with a metal. M;

(c) an 8-10-membered bicyclic ring, one of the bicyclic rings being aromatic and having a nitrogen atom member that forms a bond with a metal. M;

(d) an —$NH_2$ group whose nitrogen atom forms a bond with the metal; or (e) a —COOH group, one of whose oxygen atoms forms a bond with a metal, M.

In another embodiment, the organic molecule has:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru; or (e) a —COOH group, one of whose oxygen atoms forms a bond with Ru.

In a related embodiment, the Photolabile Compounds are useful for releasing an organic molecule, such as a drug, pharmaceutical, small biologically active molecule, and the like as described above. Release of the organic molecule from the Photolabile Compound allows the organic molecule to become bioavailable to a subject, or patient, afflicted with a disease, disorder, pathology, or condition. The Photolabile Compounds and organic molecules are useful in veterinary and human medicine. Diseases, disorders, pathologies, or conditions for which making an organic molecule bioavailable would serve to treat, ameliorate, reduce, eliminate, abate, or prevent the disease, disorder, pathology, or condition are further described below and include, as nonlimiting examples, peripheral and central nervous system disorders, neurological disorders and disorders related thereto, neurodegenerative disorders and disorders related thereto, epilepsy, seizures, migraines, headaches, stroke, anxiety, depression, restricted brain function, addictive disorders, neuroses, psychoses, pruritic conditions, Parkinson's disease, Huntington's chorea, cognitive disorders, memory lapses, Alzheimer's disease, dementia, dyskinesia, muscle spasms, retinopathy, vomiting, cancers, neoplasms, tumors, vascular diseases, and cardiovascular diseases.

As further, yet non-limiting examples, the organic molecule is a neurochemical that blocks potassium channels for use, for example, in treating neurodegenerative, or neurological diseases or disorders. In a particular embodiment, the organic molecule is 4-AP, which is a calcium channel blocker. In another embodiment, the organic molecule is TzGly, which is an NMDA-receptor agonist that is more potent than NMDA. In one embodiment, for making an organic molecule of the invention bioavailable to a subject in need thereof, the exposure of the Photolabile Compound to light can occur at the site of the disease, disorder, pathology, or condition, such as a site of a tumor, neoplasm, or cancer lesion or growth, thereby releasing the organic molecule locally and more precisely at the needed location.

In other related embodiments, the present invention provides methods for treatment, therapy, and prophylaxis by administering an effective amount of a Photolabile Compound, or a physiologically acceptable composition comprising a Photolabile Compound to a subject, so as to make an organic molecule bioavailable to the subject. The Photolabile Compound can be substantially purified (e.g., substantially free from substances that limit its effect or produce undesired side-effects). Advantageously, for methods in which a Photolabile Compound is administered to a subject, the light, e.g., infrared, laser, or visible light, for photoreleasing the organic molecule to make it bioavailable to the subject can be directed to an internal site or region of interest by using photooptic devices, probes and fibers, such as are known in the art and described supra. Those having skill in the art can employ, manipulate, and internally direct the devices for exposing a Photolabile Compound to light after the Photolabile Compound is administered to a subject.

In the methods of the present invention involving subjects, and/or the treatment, therapy, or prophylaxis of a disease, disorder, pathology, or condition, the subject is preferably an animal, including but not limited to, mammals such as human and non-human primates, cows, pigs, horses, goats, sheep, rabbits, chickens, cats, dogs, guinea pigs, rats, mice, etc. The methods of the invention especially encompass human treatments.

Various delivery systems are known and can be used to administer a Photolabile Compound, e.g., in sterile solution, encapsulation in liposomes, microparticles, microcapsules, or receptor-mediated endocytosis (See, e.g., Wu and Wu, 1987, *J. Biol. Chem.,* 262:4429-4432). Methods of introduction include, but are not limited to, intradermal, intramuscular, intraperitoneal, intravenous, subcutaneous, intranasal, epidural, topical, transdermal, parenteral, intrathecal, vaginal, rectal, colorectal, oral, intracranial, retroorbital, intrasternal routes, or a combination thereof.

The Photolabile Compounds or compositions may be administered by any convenient route or mode, for example, by continuous infusion, non-continuous infusion, or bolus injection, by absorption through epithelial or mucocutaneous linings (e.g., oral mucosa, epidermis, rectal and intestinal mucosa, etc.) and may be administered together with other biologically active and/or therapeutic agents. Administration can be systemic or local. In addition, it may be desirable to introduce the Photolabile Compounds or compositions into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a particular embodiment, it may be desirable to administer the Photolabile Compounds or compositions locally to the area in need of treatment. This may be achieved, for example, by local infusion during surgery, topical application, e.g., in conjunction with a wound dressing after surgery, by injection, by means of a catheter, by means of a suppository, or by means of an implant, where the implant is a porous, non-porous, or gelatinous material, including membranes, such as sialastic membranes, or fibers.

In another embodiment involving topical administration, a transdermal patch can be used. In accordance with this embodiment, the Photolabile Compound remains unexposed to light until the patch is manipulated by a patient or medical provider so that all or a portion of the patch containing a Photolabile Compound is exposed to light. Accordingly, the patch can be opened and the bioactive molecule released, or "activated" from the compound after exposure to light, for example, by the patient's moving from a dark room to a lighted room, or from a dark area to a light area; by the patient's directly exposing the patch, or a portion thereof, to a suitable light source, or by the patient's exposing all or a portion of the patch to daylight. A variety of types of transdermal patches are known and used by the skilled practitioner in the art. Alternatively for topical administration, a Photolabile Compound can be formulated into a light-sensitive composition, which is contained in a dark, light-protected container, and applied topically to the area of interest, e.g., applied to or rubbed onto the skin of a subject, in the dark. Following topical application in the dark, the area of interest is exposed to light, or to an appropriate light source, or the subject moves into the light, thereby causing the organic molecule of the Photolabile Compound to be released.

In another embodiment, the Photolabile Compounds or compositions can be delivered in a vesicle, in particular a liposome (See, e.g., Langer, 1990, *Science,* 249:1527-1533; Treat et al., In: Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.) In yet another embodiment, the Photolabile Compounds or compositions can be delivered in a controlled-release system. For example, a pump may be used (see Langer, supra; Sefton, 1987, *CRC Crit. Ref. Biomed. Eng.* 14:201; Buchwald et al., 1980, *Surgery,* 88:507; Saudek et al., 1989, *NEJM,* Med. 321:574 (1989)), or polymeric materials can be used (See, e.g., Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.,* 23:61; Levy et al., 1985, *Science,* 228:190; During et al., 1989, *Neurol.,* 25:351; and Howard et al., 1989, *J. Neuro-* surg., 71:105). Moreover, a controlled-release system can be placed proximal to the therapeutic target, e.g., the brain, thus requiring only a fraction of the systemic dose (see, e.g., Goodson, 1984, In: Medical Applications of Controlled Release, Vol. 2, pp. 115-138). As further guidance, other controlled release systems are found in Langer, 1990, Science, 249:1527-1533.

The Photolabile Compounds are also provided in effective amounts in pharmaceutical compositions comprising a pharmaceutically acceptable carrier, diluent, excipient, or vehicle, for example, for use as therapeutics. In one embodiment, the term "pharmaceutically acceptable" refers to approval by a regulatory agency of the Federal or a state government, or listed in the U.S. Pharmacopeia or other generally recognized pharmacopeia for use in animals, and more particularly, in humans. The terms vehicle, carrier, or excipient refer to a diluent or adjuvant in or with which the therapeutic is administered. Such pharmaceutical carriers, vehicles, or excipients can be sterile liquids, such as water and oils, including those of petroleum, animal, vegetable or synthetic origin, e.g., peanut oil, soybean oil, mineral oil, sesame oil and the like. Water is a preferred carrier when a pharmaceutical composition is administered intravenously and is water soluble. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. If needed or desired, the composition of the invention can also contain minor amounts of wetting or emulsifying agents, or pH buffering agents.

The Photolabile Compounds and compositions of the present invention can be formulated as solutions, suspensions, emulsions, tablets, pills, capsules, powders, sustained-release formulations and the like. The compositions can be formulated as a suppository, with traditional binders and carriers such as triglycerides. Oral formulations can include standard carriers, such as pharmaceutical grades of mannitol, lactose, starch, magnesium stearate, sodium saccharine, cellulose, magnesium carbonate, etc. Examples of suitable pharmaceutical carriers and the like are described in the current edition of "Remington's Pharmaceutical Sciences" by E. W. Martin. Such compositions routinely contain a therapeutically effective amount of the Photolabile Compound, preferably in purified form, together with a suitable amount of carrier so as to provide the form for proper administration to a subject. The formulation should suit the mode of administration.

In another embodiment, a Photolabile Compound of the invention is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container, such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Sterility for of a composition for therapeutic administration is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle. Therapeutics are typically stored in unit or multi-dose containers, for example, sealed ampoules or vials, as an aqueous solution or as a lyophilized formulation for reconstitution. Where necessary, the ampoule or vial is essentially impenetrable by light. As an example of a lyophilized therapeutic formulation, 10-ml vials are filled with 5 ml of sterile-filtered 1% (w/v) aqueous therapeutic solution, and the resulting mixture is lyophilized. The infusion solution is prepared by reconstituting the lyophilized therapeutic using bacteriostatic Water-for-Injection.

The amount of a Photolabile Compound which will be effective in the treatment, amelioration, reduction, elimination, inhibition, or prevention of a particular disease, condition, pathology, or disorder associated with the use and bioactivity of an organic molecule can be determined by standard clinical techniques. An "effective amount" or a "pharmaceutically effective amount" of a Photolabile Compound of this invention refers to an amount effective for treating, ameliorating, reducing, abating, eliminating, preventing, a disease, condition, pathology, or disorder for which the compound is being used. In particular embodiments, an effective amount is an amount effective for making an organic molecule of the invention bioavailable to a subject. If another therapeutic agent is used in conjunction with the Photolabile Compounds, the effective amount of the therapeutic agent refers to an amount effective for providing the therapeutic effect of the therapeutic agent. The precise dose to be employed in the formulation will also depend on the route of administration, as well as an individual patient's circumstances, such as age, health and vital statistics of the patient, and the severity of the disease, condition, or disorder. Dosing should be decided according to the judgment of the medical practitioner based on an evaluation of the patient and considerations of a patient's physiologic situation and medical history. In addition, in vitro assays may optionally be used to assist in determining optimal dosage ranges. Effective doses can be extrapolated from dose-response curves derived from in vitro or in vivo animal model test systems.

As general guidance, the total effective amount of a Photolabile Compound administered parenterally per dose will be in the range of about 1 µg/kg/day to 10 mg/kg/day of a subject's body weight, although, as noted above, this will be subject to discretion based on the subject's condition and the above-mentioned variables. A therapeutic dose can also be at least 0.01 mg/kg/day, or between about 0.01 and 1 mg/kg/day, with particular regard for human administration. If given continuously, a therapeutic is typically administered at a dose rate of about 1 µg/kg/hour to about 50 µg/kg/hour, either by 1 to 4 injections per day or by continuous subcutaneous infusions, e.g., using a mini-pump. An intravenous bag solution may also be employed. The length of treatment needed to observe changes and the interval following treatment for responses to occur will likely vary depending on the desired effect. In some embodiments, suitable effective dosage amounts range from about 10 µg to about 2500 mg about every 4 hours, although the amounts are typically about 100 mg or less. In one embodiment, the effective dosage of a Photolabile Compound ranges from about 0.01 mg to about 100 mg about every 4 hours. In another embodiment, the effective dosage of a compound of the invention ranges from about 0.020 mg to about 50 mg every 4 hours, and in another embodiment, about 0.025 mg to about 20 mg about every 4 hours. The effective dosage amounts refer to total amounts administered. Thus, if more than one of the Photolabile Compounds is administered, the effective dosage amounts correspond to the total amount administered.

In another embodiment, if a Photolabile Compound is contacted with a biological sample in vitro, an effective amount will typically range from about 0.01 µg/L to about 5 mg/L; in another embodiment from about 0.01 µg/L to about 2.5 mg/L; in another embodiment, from about 0.01 µg/L to about 0.5 mg/L; and in yet another embodiment, from about 0.01 µg/L to about 0.25 mg/L of a solution or suspension of a pharmaceutically acceptable carrier, diluent, or excipient. In an embodiment, the volume of solution or suspension is from about 1 µL to about 1 mL; in another embodiment, the volume of solution or suspension is about 200 µL.

Examples of neoplastic or hyperproliferative diseases, disorders, pathologies, or conditions that can be treated, ameliorated, reduced, abated, eliminated, inhibited, prevented, and/or diagnosed using the Photolabile Compounds and photoreleased organic molecules include, but are not limited to, neoplasms (cancers or tumors) located in the colon, abdomen, bone, breast, digestive system, esophagus, liver, pancreas, peritoneum, endocrine glands (adrenal, parathyroid, pituitary, testicles, ovaries, cervix, thymus, thyroid), eye, head and neck, nervous (central and peripheral), lymphatic system, pelvis, skin, soft tissue, spleen, thoracic areas, bladder, and urogenital system. Cancers that may be treatable using the Photolabile Compounds include follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer, or metastases thereof. Autoimmune diseases, disorders, or conditions may be treatable with the Photolabile Compounds and include multiple sclerosis, Sjogren's syndrome, Hashimoto's thyroiditis, biliary cirrhosis, Bechet's disease, Crohn's disease, polymyositis, systemic lupus erythematosus and immune-related glomerulonephritis, rheumatoid arthritis, ischemic injury (e.g., caused by myocardial infarction, stroke and reperfusion injury), liver injury (e.g., hepatitis related liver injury, ischemia/reperfusion injury, cholestosis (bile duct injury) and liver cancer); toxin-induced liver disease (e.g., caused by alcohol), septic shock, cachexia and anorexia. Viral infections (such as herpes viruses, pox viruses and adenoviruses), inflammation, graft versus host (GVH) disease, acute graft rejection, and chronic graft rejection may also be treatable with the Photolabile Compounds.

Additional diseases or conditions associated with abnormal and increased cell survival that may be treated, ameliorated, reduced, abated, eliminated, inhibited, prevented, and/or diagnosed using the Photolabile Compounds include, but are not limited to, progression and/or metastases of malignancies and related disorders such as leukemia (including acute leukemias (e.g., acute lymphocytic leukemia, acute myelocytic leukemia, including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In another embodiment, the Photolabile Compounds may be needed as therapeutics to stimulate epithelial cell proliferation and basal keratinocytes for the purpose of wound healing, and to stimulate hair follicle production and the healing of dermal wounds. The Photolabile Compounds of the invention may be clinically useful in stimulating wound healing, including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment using steroids, radiation therapy, anti-neoplastic drugs and anti-metabolites.

Other diseases, disorders, or conditions that may be treated, ameliorated, reduced, abated, eliminated, inhibited, prevented, and/or diagnosed with the Photolabile Compounds include AIDS; neurodegenerative diseases, disorders, and/or conditions (such as Alzheimer's disease, Parkinson's disease, amyotrophic lateral sclerosis (ALS), multiple sclerosis, Retinitis pigmentosa (RP), cerebellar degeneration and brain tumor or prior associated disease).

In one embodiment, diseases and conditions that are treatable using calcium channel blockers, e.g., 4AP, include without limitation, heart disease, hypertension, angina, chest pain, cardiovascular diseases, such as coronary artery disease, cardiomyopathies, valvular heart disease, renal disease, Peyronie's disease and neurological, neurophysiological, or neuromuscular diseases and conditions, e.g., amyotrophic lateral sclerosis (ALS), multiple sclerosis.

In another embodiment, diseases that are treatable using NMDA receptor agonists or antagonists, e.g., TzGly, include without limitation, neurological, neurodegenerative, or neurophysiological diseases, disorders, and conditions, such as Alzheimer's disease, Parkinson's disease, Huntington's disease, and dyskinesias. In another embodiment, neurological, neurodegenerative, and neurophysiological diseases, e.g., Parkinson's disease, Alzheimer's disease, etc., are treatable using Tz-AMPA.

In another embodiment, the present invention relates to kits comprising a Photolabile Compound and instructions for use. A kit may be used in a diagnostic, screening, or testing assay. A kit may also be a pharmaceutical pack, particularly for use in treating or preventing a disease, disorder, pathology, or condition. A kit for pharmaceutical use is typically sterile and contains a Photolabile Compound in an amount effective to treat or prevent a disease, disorder, pathology, or condition, and a pharmaceutically acceptable carrier, diluent, or excipient. The kit, or a pharmaceutical pack, can comprise one or more vessels or containers filled with an effective amount, e.g., unit dosage form, of one or more of the Photolabile Compounds or compositions of the invention, and a pharmaceutically acceptable carrier, diluent, or excipient. The kit, or pharmaceutical pack, can further comprise a label. In addition, the kit, or pharmaceutical pack, can also include a unit dosage form of another therapeutic agent, for example, a container containing an effective amount of the other therapeutic agent. The kit, or pharmaceutical pack, may further optionally contain a notice in the form prescribed by a governmental agency regulating the manufacture, use, or sale of pharmaceuticals or biological products, reflecting approval by the agency of manufacture, use or sale for human administration. The kit, or pharmaceutical pack, can also contain a device useful for administering the unit dosage forms. Examples of such devices include, without limitation, a syringe, a drip bag, a patch, an inhaler, and an enema bag or container.

EXAMPLES

The examples described below are provided to illustrate the present invention and are not included for the purpose of limiting the invention.

Example 1

Synthesis of $[Ru(bpy)_2(4AP)_2]Cl_2$ 159 mg of $Ru(bpy)_2Cl_2$, where bpy=2,2'-bipyridine, were suspended in 7 mL of water at 85° C. under $N_2$. After dissolution, 66 mg of 4-aminopyridine ("4AP") were added, and the resultant solution was heated for about 20 minutes at about 50-80° C. or greater. A molar excess of $NH_4PF_6$, was added, and the resultant red solid was washed with water and dried. The red solid was dissolved in a minimal amount of acetone, and to the acetone solution was added tetraethylammonium chloride, precipitating $[Ru(bpy)_2(4AP)_2]Cl_2$ (79% yield).

Example 2

Synthesis of $[Ru(bpy)_2(TzGly)_2]Cl_2$ $[Ru(bpy)_2(TzGly)_2]Cl_2$ was made according to the procedure used to make $[Ru(bpy)_2(4AP)_2]Cl_2$ set forth in Example 1, except that (RS)-(tetrazol-5-yl)glycine ("TzGly") was used in place of 4AP.

Example 3

Synthesis of $[Ru(bpy)_2(5HT)_2]Cl_2$ $[Ru(bpy)_2(5HT)_2]Cl_2$ is made according to the procedure used to make $[Ru(bpy)_2(4AP)_2]Cl_2$ set forth in Example 1, except that serotonin ("5HT") is used in place of 4AP.

Example 4

Synthesis of $[Ru(bpy)_2(4AP)(PPh_3)]Cl_2$ $Ru(bpy)_2Cl_2$, where bpy=2,2'-bipyridine, was suspended in water at a concentration of 10 mg/mL at 85° C. under $N_2$. After dissolution, 1 equivalent of $PPh_3$ was added, and the resultant solution was heated for about 60 minutes at about 50-80° C. or greater. 1.1 Equivalents of 4AP were subsequently added, and heating continued for an additional 30 minutes. A molar excess of $NH_4PF_6$, was added, and the resultant orange solid was washed with water and dried. The orange was dissolved in a minimal amount of acetone, and to the acetone solution was added tetraethylammonium chloride, precipitating $[Ru(bpy)_2(4AP)(PPh_3)]Cl_2$.

Example 5

Synthesis of $[Ru(bpy)_2(TzGly)(PPh_3)]Cl_2$ $[Ru(bpy)_2(TzGly)(PPh_3)]Cl_2$ was made according to the procedure used to make $[Ru(bpy)_2(4AP)(PPh_3)]Cl_2$ set forth in Example 4, except that TzGly was used in place of 4AP.

Example 6

Synthesis of $[Ru(bpy)_2(5HT)(PPh_3)]Cl_2$ $[Ru(bpy)_2(5HT)(PPh_3)]Cl_2$ is made according to the procedure used to make $[Ru(bpy)_2(4AP)(PPh_3)]Cl_2$ set forth in Example 4, except that serotonin is used in place of 4AP.

Example 7

Synthesis of $[Ru(bpy)_2(nicotine)(PPh_3)]Cl_2$ $[Ru(bpy)_2(nicotine)(PPh_3)]Cl_2$ is made according to the procedure used to make $[Ru(bpy)_2(4AP)(PPh_3)]Cl_2$ set forth in Example 4, except that nicotine is used in place of 4AP.

Example 8

Synthesis of $[Ru(bpy)_2(TzGly)(py)]Cl_2$ $[Ru(bpy)_2(TzGly)(py)]Cl_2$, where py=pyridine, was made according to the procedure used to make $[Ru(bpy)_2(4AP)(PPh_3)]Cl_2$ set forth in Example 4, except that TzGly was used in place of 4AP and pyridine was used in place of $PPh_3$.

Example 9

Synthesis of $[Ru(bpy)_2(4AP)(py)]Cl_2$ $[Ru(bpy)_2(4AP)(py)]Cl_2$, where py=pyridine, is made according to the procedure used to make $[Ru(bpy)_2(4AP)(PPh_3)]Cl_2$ set forth in Example 4, except that pyridine is used in place of $PPh_3$.

Example 10

Synthesis of $[Ru(bpy)_2(5HT)(py)]Cl_2$ $[Ru(bpy)_2(5HT)(py)]Cl_2$, where py=pyridine, is made according to the procedure used to make $[Ru(bpy)_2(4AP)(PPh_3)]Cl_2$ set forth in Example 4, except that 5HT is used in place of 4AP and pyridine is used in place of $PPh_3$.

Example 11

Synthesis of [Ru(bpy)$_2$(nicotine)(py)]Cl$_2$

[Ru(bpy)$_2$(nicotine)(py)]Cl$_2$, where py=pyridine, is made according to the procedure used to make [Ru(bpy)$_2$(4AP)(PPh$_3$)]Cl$_2$ set forth in Example 4, except that nicotine is used in place of 4AP and pyridine is used in place of PPh$_3$.

Example 12

Synthesis of Co(DMG)$_2$(5HT)(Cl)

CoCl$_2$ was dissolved in a 1:1 v/v mixture of water/ethanol at a final concentration of about 0.2 M. Two equivalents of dimethylglyoxime ("DMG") were added, and the resultant mixture was allowed to stir under N$_2$ until dissolution. One equivalent of 5HT was added, air was bubbled into the resultant mixture for 6 hours and Co(DMG)$_2$(5HT)(Cl) precipitated. The precipitated product was filtered and washed.

Example 13

Photorelease of 4AP from [Ru(bpy)$_2$(4AP)$_2$]Cl$_2$

UV-vis spectra in water were obtained with an HP 8453 diode array spectrophotometer. RMN $^1$H spectra were obtained using a Bruker 500 MHz equipment. CV measurements were performed with a PAR 273A potentiostat. Irradiation was effected by means of a pulsed Xe lamp, (pulse energy ~0.5 J), with a low-pass filter at 480 nm. Irradiation using a 473 nm DPSS laser gave similar results.

[Ru(bpy)$_2$(4AP)$_2$]Cl$_2$ is very soluble in water and stable in the dark, while undergoing decomposition under irradiation with visible light in its metal-to-ligand charge transfer (MLCT) band, centered at 489 nm. (In CH$_3$CN solution, the absorption band is red-shifted to 492 nm, consistent with the lower polarity of the solvent, despite a previous characterization that reported 450 nm. However, light exposure of a CH$_3$CN solution of [Ru(bpy)$_2$(4AP)$_2$]Cl$_2$ produced a yellow compound with absorption maximum at 450 nm. This may correspond to the previously misinterpreted assignments for this compound (D. Chun-Ying et al., 1999, *J. Coord. Chem.*, 46:301-312), and the photoproduct is likely to be the complex [Ru(bpy)$_2$(4AP)CH$_3$CN]$^{2+}$). Several ruthenium polypyridyl complexes present this behavior. (D. V. Pinnick et al., 1984, *Inorg. Chem.*, 23:1440-1445).

Although at pH 7 the spectrum of the irradiated complex is very similar to that of the original complex, a diminished shoulder at 470 nm becomes evident. To determine the nature of the photoreaction, NMR spectra were taken before and after irradiation with visible light. FIG. 1 shows the signal assigned to the meta hydrogens [Ru(bpy)$_2$(4AP)$_2$]Cl$_2$ (m1). After irradiation, this signal decreased, and two new signals appeared at lower fields: one corresponding to the free ligand (m3), and the other corresponding to the aquo-4AP complex (m2), indicating photorelease of the 4AP. These two latter signals integrated for 0.30 and 0.27 of the initial signal, which corresponds to a photoreaction of 60%.

The redox potential of the couple Ru$^{III}$/Ru$^{II}$ for [Ru(bpy)$_2$(4AP)$_2$]Cl$_2$ measured in water is E=0.76 V versus Ag/AgCl, which is consistent with the higher basicity of 4AP compared with that of pyridine. Thus, the redox and the photochemistry of [Ru(bpy)$_2$(4AP)$_2$]Cl$_2$ is in total agreement with results obtained corresponding to the Ru(bpy)$_2$XY family, X and Y being monodentate ligands. (See, e.g., E. S. Dodsworth et al., 1986, *Chem. Phys. Lett.*, 124:152-158). The photoactivity of these compounds has been explained in terms of a reaction pathway that involves the transition between the MLCT state to a lower-energy d-d state, which promotes ligand release. There is a direct correspondence between the energy of the MLCT transition and the quantum yield of the photoreaction. For [Ru(bpy)$_2$(4AP)CH$_3$CN]$^{2+}$, the photoreaction yield is about $\phi_{PR}$=0.4. Since [Ru(bpy)$_2$(4AP)$_2$]Cl$_2$ presents a red-shifted band, a lower photoreaction yield is expected. An estimate based on early experiments leads to an estimate of $\phi_{PR}\cong$0.02 at 473 nm.

Example 14

Neurophysiological Activity of 4AP Photoreleased from [Ru(bpy)$_2$(4AP)$_2$]Cl$_2$ A standard setup for intracellular voltage measurements was used, and the medicinal leech *Hirudo medicinalis* was used to demonstrate photoreleased 4AP's neurophysiological activity. *Hirudo medicinalis* has a central nerve cord with several ganglia, each one containing about 400 neurons arranged in a known pattern. (W.-R. Schlue et al., 1980, *J. Exp. Biol.*, 82:23-34). An entire ganglion was mounted on a dish. The transmembrane potential for a single cell (a neuron) in the ganglion was recorded by inserting inside the neuron a glass micropipet with a micrometer-sized end, filled with saturated aqueous KCl that acts as a luggin bridge for an Ag/AgCl electrode. Another Ag/AgCl electrode was used as a reference. The signal was taken with an AM-System 1600 amplifier, and the entire setup was covered with a Faraday cage. A 12 bit A/D acquisition card was used to digitize the data using an ad-hoc program written in QuickBasic.

Figure 2:
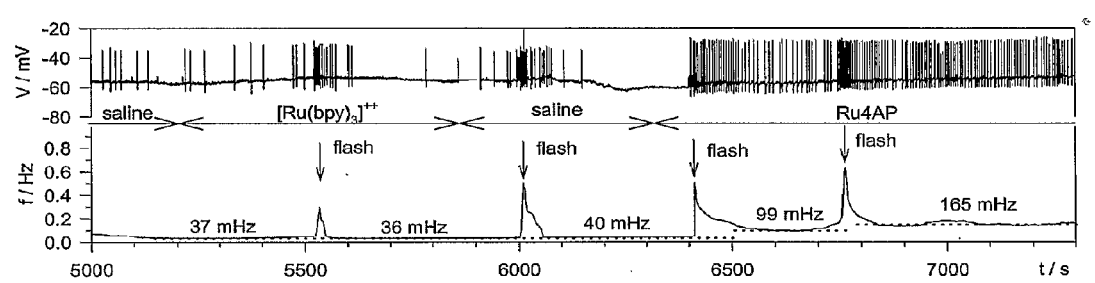
FIG. 2 (Top) shows action potentials (spikes) recorded in a medicinal leech (Hirudo medicinalis) neuron for saline and solutions of [Ru(bpy)$_3$]Cl$_2$ and [Ru(bpy)$_2$(4AP)$_2$]Cl$_2$ (Bottom): Frequency of the spikes. Arrows indicate irradiation with Xe flashlamp. (Middle): Composition of the extracellular medium.
Figure 3:
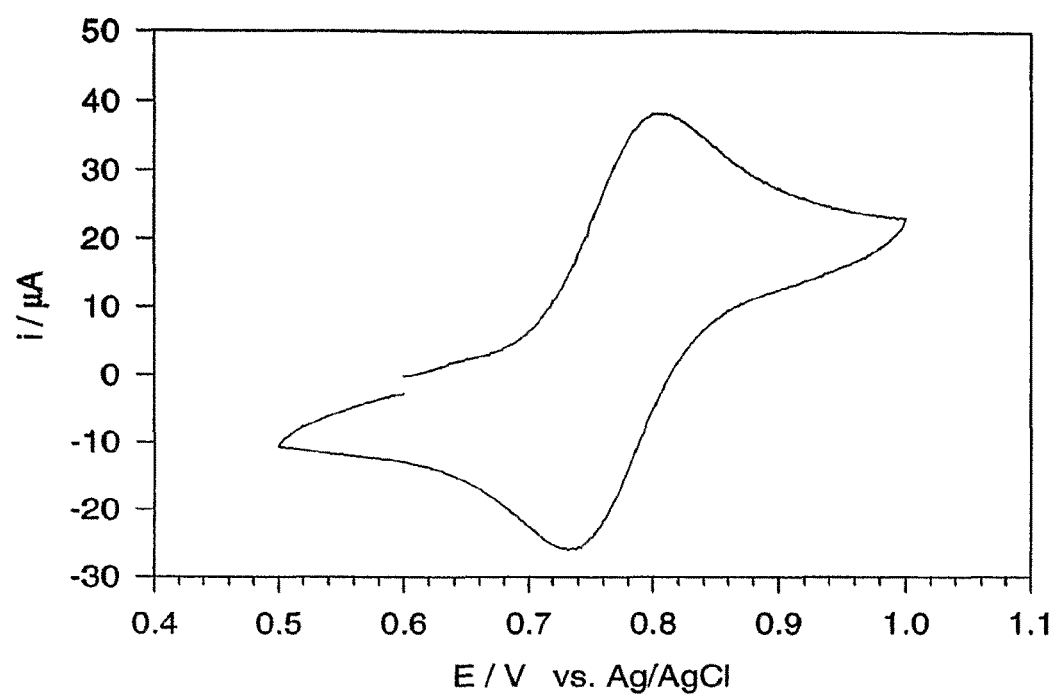
FIG. 3 shows cyclic voltammetry (CV) profile of [Ru(bpy)$_2$(4AP)$_2$]Cl$_2$ in water. The supporting electrolyte was KNO$_3$ (1 M). dE/dt=100 mV/s in glassy carbon electrode.
Figure 4A:
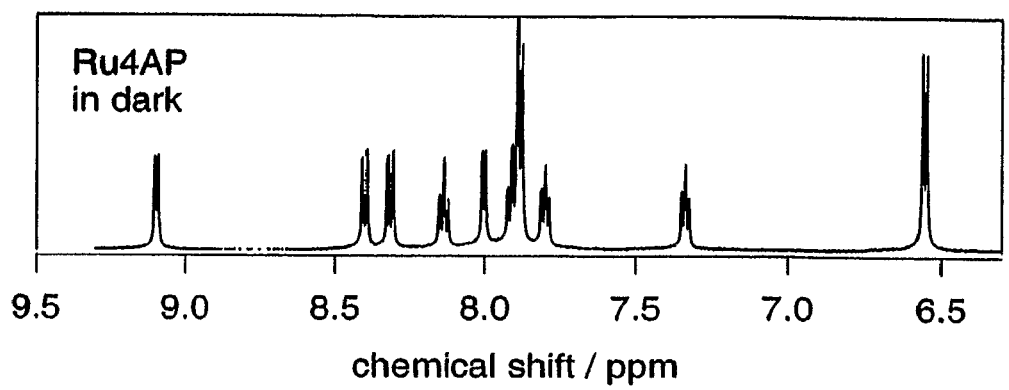
FIGS. 4A and 4B show NMR spectra of [Ru(bpy)$_2$(4AP)$_2$]Cl$_2$ in D$_2$O before (FIG. 4A) and after (FIG. 4B) irradiation. Bruker 500 MHz.
Figure 4B:
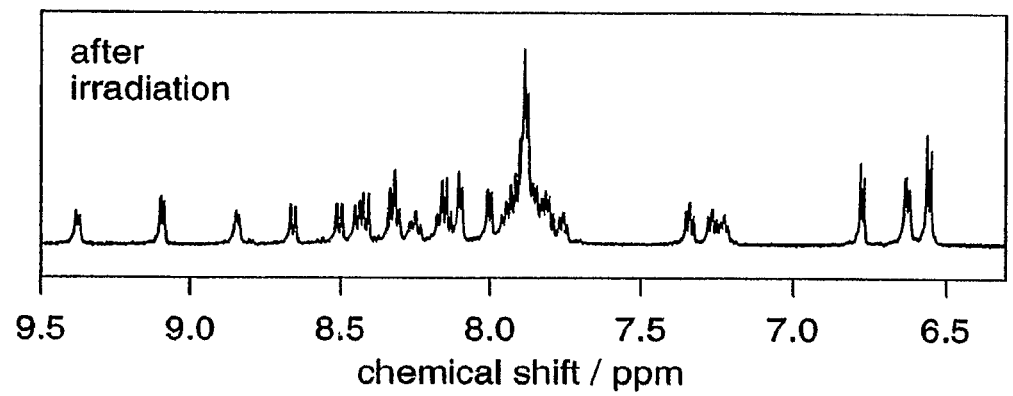
Figure 5:
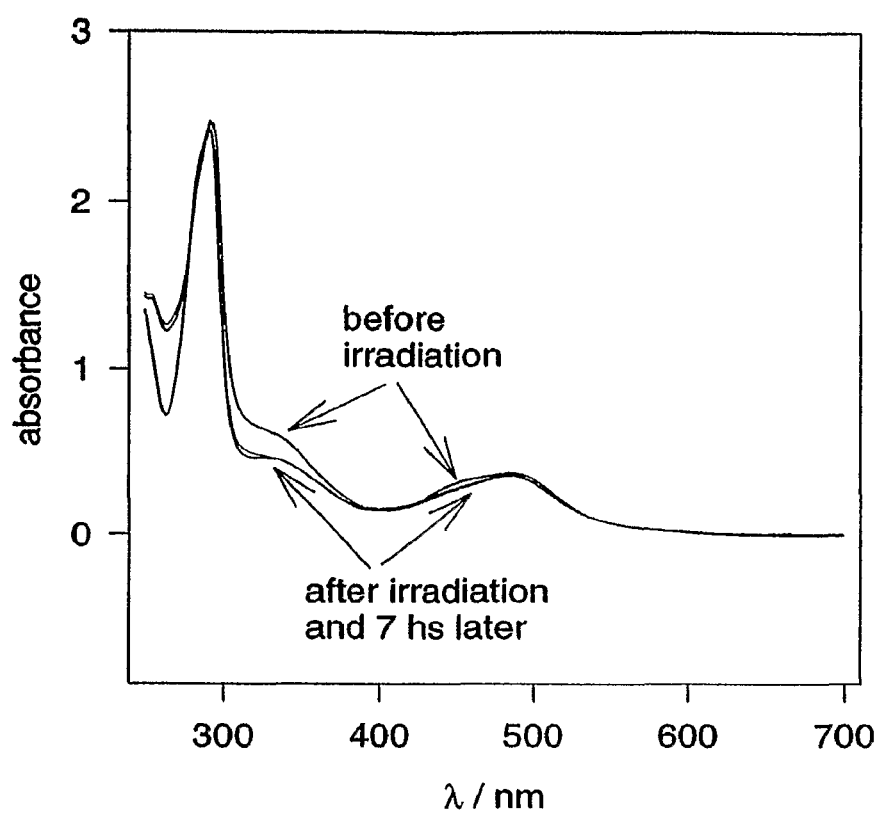
FIG. 5 shows the UV-visible (UV-vis) spectra of Ru(bpy)$_2$(4AP)$_2$ before and after complete photolysis. The photoproducts after exposure to light were Ru(bpy)$_2$(4AP)(H$_2$O) and free 4AP. The complex did not undergo dark decomposition for more than 20 hours. After 7 hours in the dark, the irradiated solution showed less than 4% of 4AP recombination.
Figure 6:
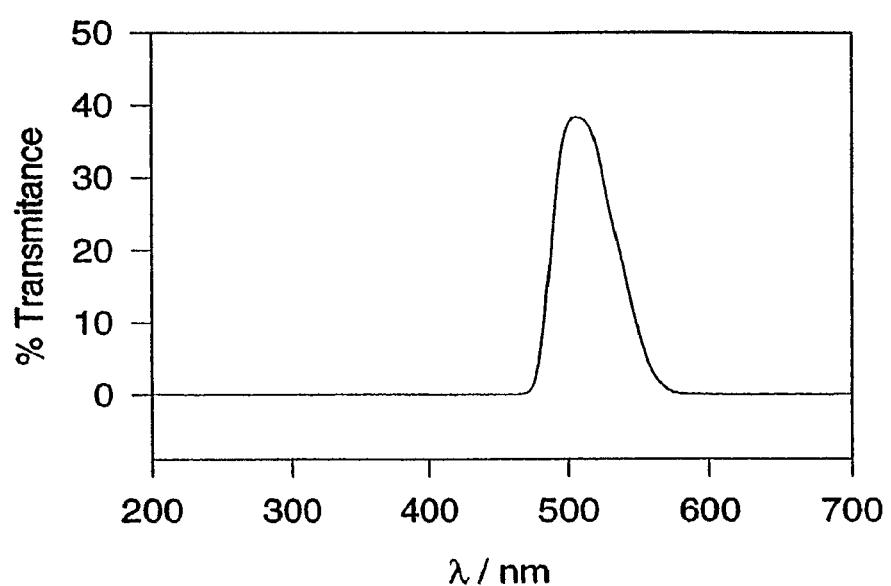
FIG. 6 shows a UV-vis spectrum of the filter used for the ganglion irradiation experiments as described in Example 3.
Figure 7A:
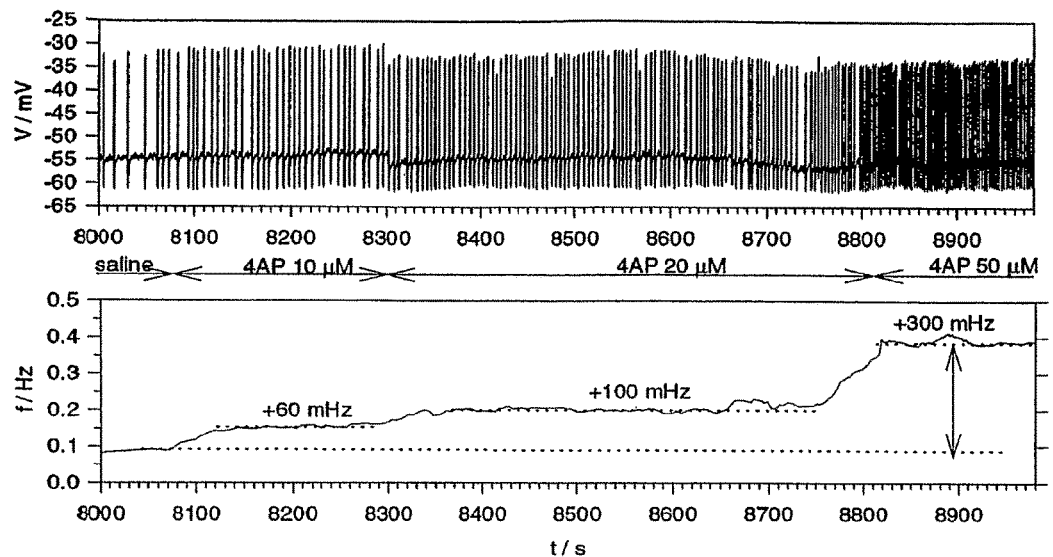
FIGS. 7A and 7B show action potentials and frequency of the spikes obtained in studies of medicinal leech (Hirudo medicinalis) ganglia.
Figure 7B:
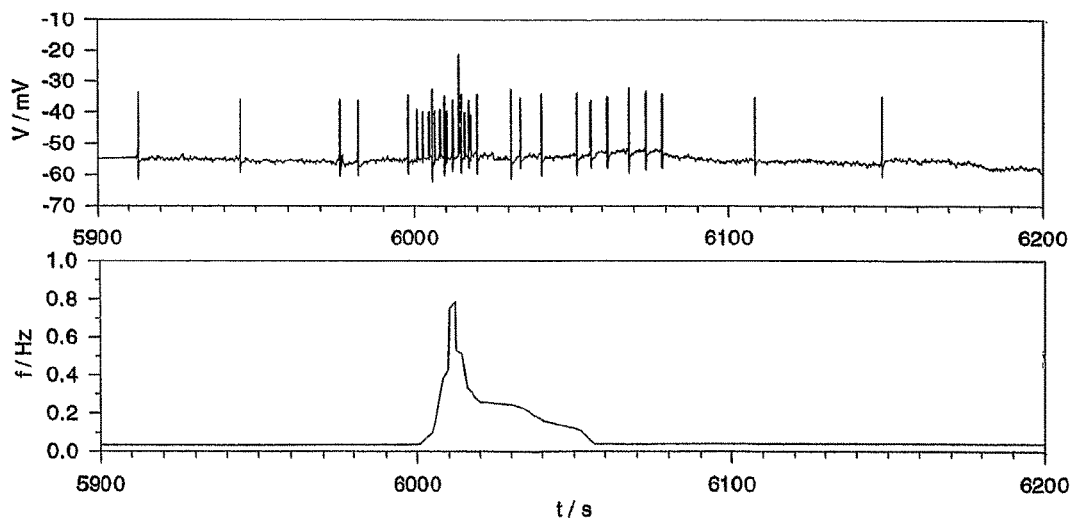
Figure 8A:
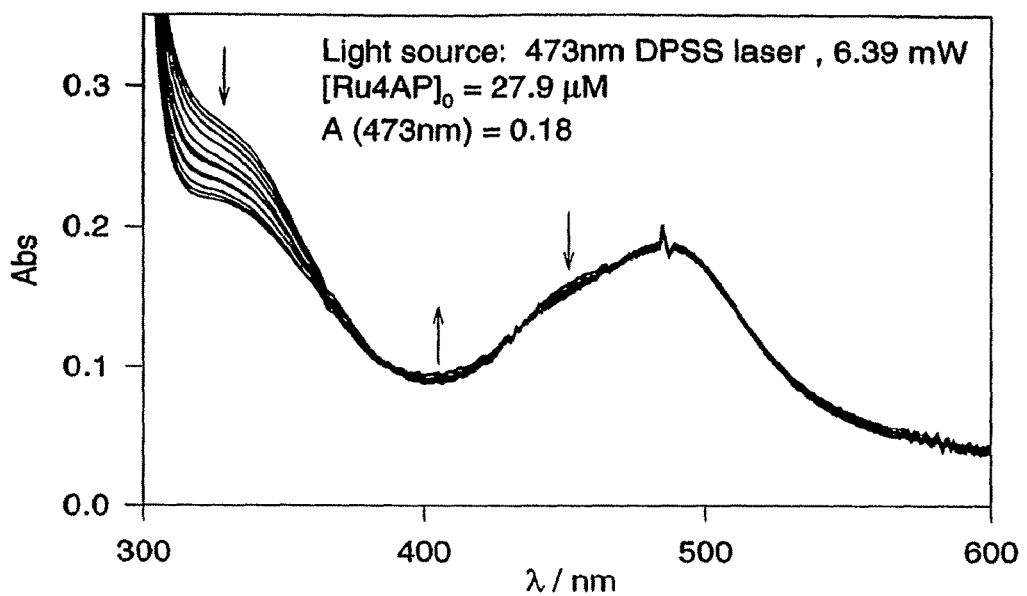
FIGS. 8A and 8B relate to spectra changes of [Ru(bpy)$_2$(4AP)$_2$]Cl$_2$ during exposure to light.
Figure 8B:
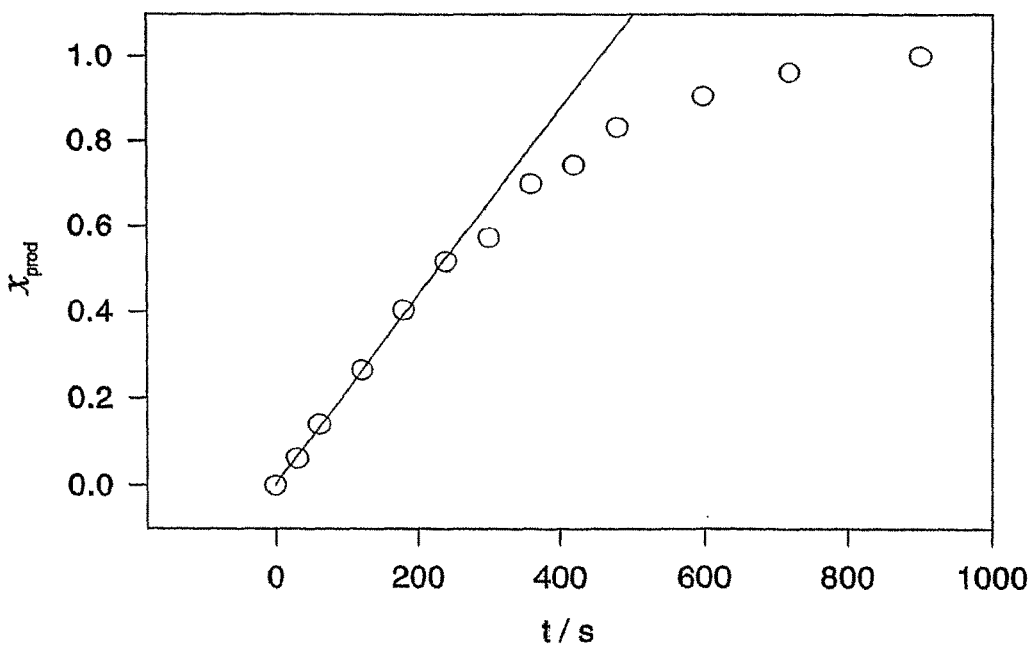
Figure 9:
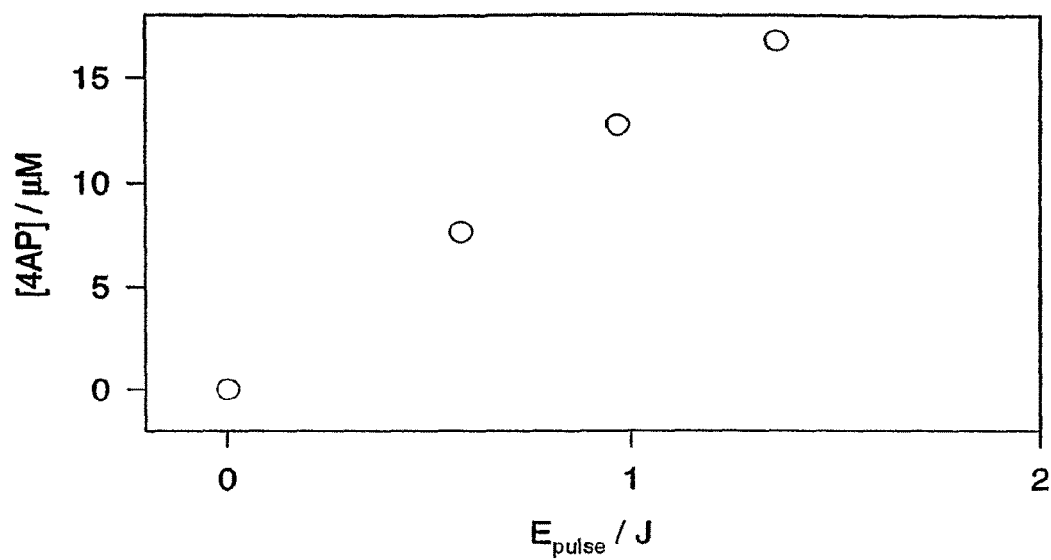
FIG. 9 shows a graph of photoreleased 4AP versus pulse energy. The light source was pulsed Xe lamp with a bandpass filter. [Ru(bpy)$_2$(4AP)$_2$]Cl$_2$=44 μM; Vol.=3 mL. The data were obtained from UV-vis spectra analysis.
Figure 10:
FIG. 10 shows several two-photon fluorescence images of [Ru(bpy)$_2$(TzGly)(py)]Cl$_2$ at different excitation wavelengths. (Magnification: ~20×).
Figure 13A:
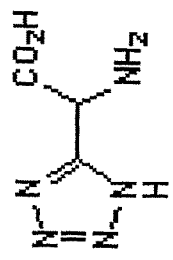
FIGS. 13A and 13B.
Figure 13B:
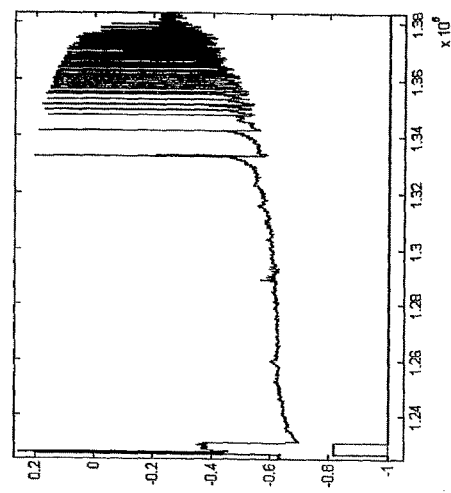
Figure 11:
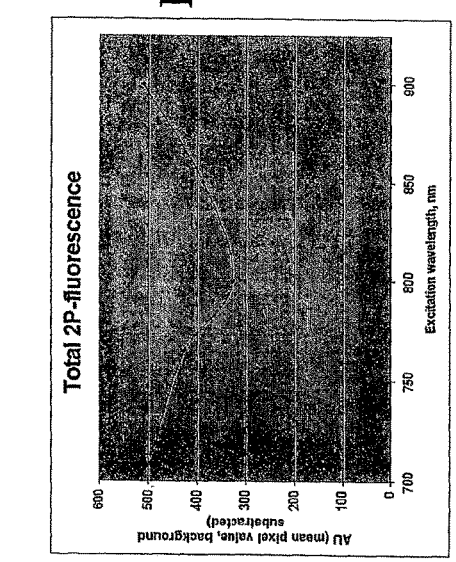
FIG. 11 depicts a graph of total two-photon fluorescence versus excitation wavelength of [Ru(bpy)$_2$(4AP)$_2$]Cl$_2$.
Figure 12:
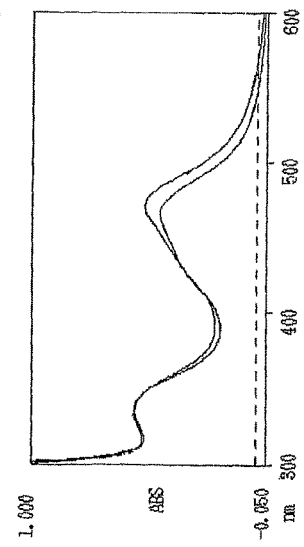
FIG. 12 presents a UV-vis spectrum of TzGly before and after irradiation with 400-600 nm light.
Figure 14A:
FIGS. 14A-G relate to experiments performed on neurons contacted with [Ru(bpy)$_2$(TzGly)(py)]Cl$_2$.
Figure 14B:
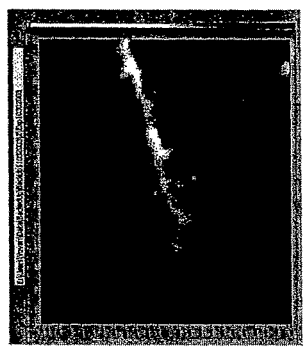
Figure 14C:
Figure 14D:
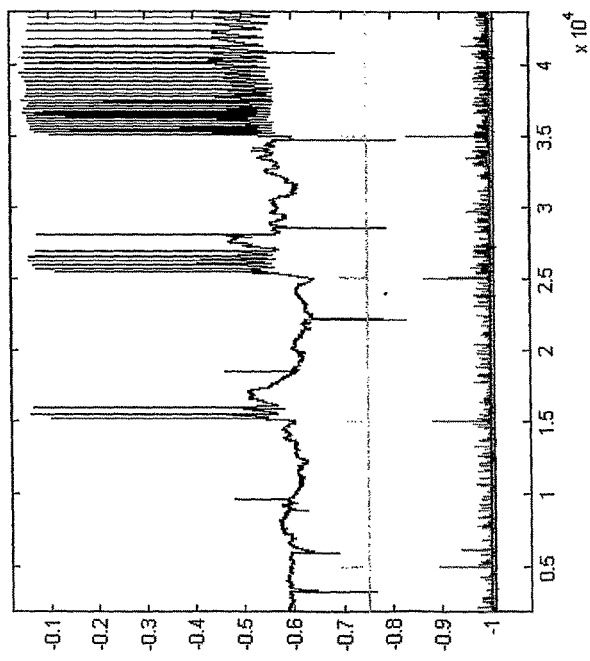
Figure 14G:
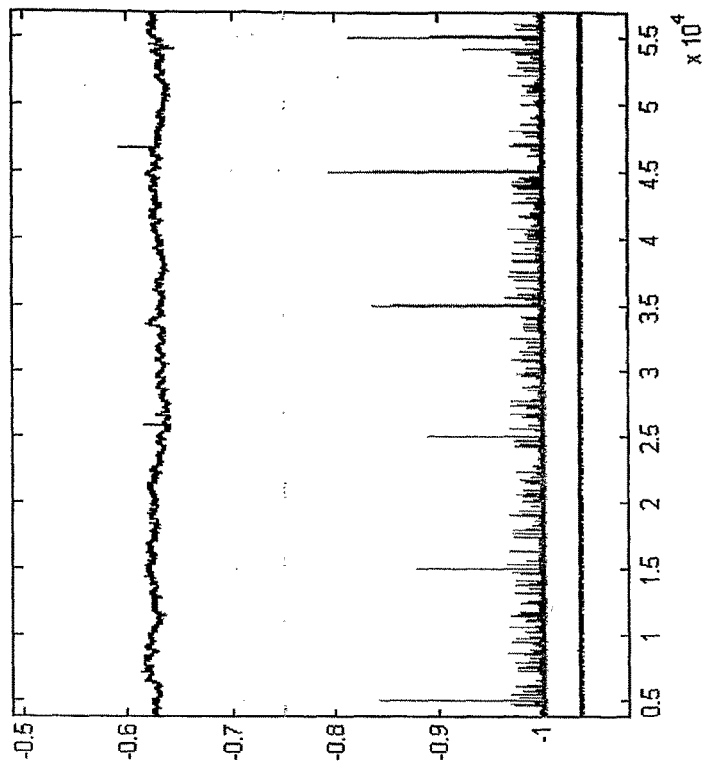
Figure 14E:
Figure 14F:
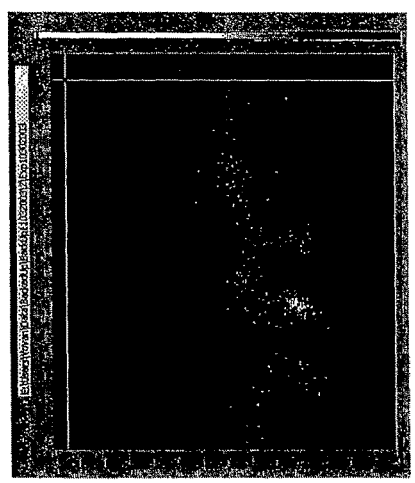

Low Ca$^{2+}$-high Mg$^{2+}$ saline solution (NaCl, 102 mM; KCl, 4 mM; CaCl$_2$: 1 mM; and MgCl$_2$: 10 mM; Tris base, pH 5.4 adjusted to 7.4) was perfused through the dish. [Ru(bpy)$_2$(4AP)$_2$]Cl$_2$ and the free ligand 4AP were injected in the mainstream at controlled times. A pulsed Xe lamp located under the dish was used to irradiate the solution. UV light was removed using a band-pass filter at 500 nm. FIG. 2 shows the behavior of the membrane potential recorded at one of the Retzius (Rz) cells in the ganglion. The upper graph in FIG. 2 shows the raw data, presenting periods of rest potential and very fast spikes (action potentials), produced by the changes in membrane ion permeabilities. The lower graph shows the instantaneous spiking frequency at each time.

After impaling the cell with an electrode, many experiments were performed on the same cell to ensure reproducibility. After 5000 seconds, the cell showed low activity, as can be seen at the left of the graph. At t=5200 s, ~100 µM Ru(bpy)$_3$Cl$_2$ was added to the saline solution, without significant changes in activity. 300 seconds later, at 5500 s, a light flash was directed to the ganglion. The sudden increase in the frequency of the action potentials is mainly due to the temperature pulse, but after a short time the activity decreased to the basal level. After washing by perfusion, further irradiation (t=6000 s) with a pulse showed a very similar pattern. At t=6250 s, ~100 µM [Ru(bpy)$_2$(4AP)$_2$]Cl$_2$ was added to the saline and the activity remained unchanged. However, after a new light flash (t=6400 s), sudden activity was recorded and it remained high after 300 s. A second light pulse at 6750 s promoted an even higher activity, which decreased only after cleaning perfusion with pure saline.

A similar frequency increase occurred when free 4AP was perfused onto the ganglion, thus demonstrating that the release of 4AP causes this maintained frequency increase. Calibration of the cell activity using solutions of 4AP showed that in each irradiation, 10-15 μM of 4AP were released from [Ru(bpy)$_2$(4AP)$_2$]Cl$_2$ during the previous experiments. Neither toxicity nor a deleterious effect was observed on the neuron during the experiments. These results show that a neuronal response can be stimulated using [Ru(bpy)$_2$(4AP)$_2$]Cl$_2$, an illustrative Photolabile Compound, to photorelease an organic molecule having neurophysiological activity.

Example 15

Photorelease of TzGly from [Ru(bpy)$_2$(TzGly)(py)]Cl$_2$

The procedure for the photorelease of TzGly from [Ru(bpy)$_2$(TzGly)(py)]Cl$_2$ is analogous to that used for photorelease of 4AP from [Ru(bpy)$_2$(4AP)$_2$]Cl$_2$ described above in Example 13, except that the irradiation light spot was very localized (diameter <1 micron). Irradiation of [Ru(bpy)$_2$(TzGly)(py)]Cl$_2$ at 470 nm photoreleased TzGly.

Example 16

Neurophysiological Activity of TzGly Photoreleased from [Ru(bpy)$_2$(TzGly)(py)]Cl$_2$ The neurophysiological activity of photoreleased TzGly was assessed by performing experiments similar to those as set forth above in Example 14. Accordingly, the standard setup for intracellular voltage measurements was used, and the medicinal leech *Hirudo medicinalis* was used to demonstrate photoreleased TzGly's neurophysiological activity in the leech ganglion.

All patent applications, published patent applications, issued and granted patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

The invention claimed is:
1. A compound of Formula IVa:

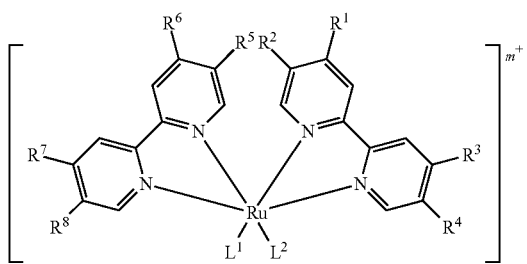

IVa wherein:
  each $L^1$ is independently an organic molecule having an amine group whose nitrogen atom forms a bond with Ru, wherein said organic molecule containing an amine group is selected from the group consisting of an amino acid, dopamine, GABA, serotonin, and aminobutyric acid;
  $L^2$ is $(R^2)_3P$, $(R^2O)_3P$, wherein each $R^2$ is independently —C$_1$-C$_{18}$ alkyl, or phenyl, and m is 2;
  $R^1$ to $R^8$ are independently —H, —C$_1$-C$_{18}$ alkyl; —NH$_2$, —COOH, —(C$_1$-C$_{18}$ alkyl)-O—(C$_1$-C$_{18}$ alkyl), or —OC(O)(C$_1$-C$_{18}$ alkyl); and
  X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$.

2. The compound of claim 1, wherein the organic molecule is an amino acid.

3. The compound of claim 1, wherein the organic molecule is dopamine.

4. The compound of claim 1, wherein the organic molecule is GABA.

5. The compound of claim 1, wherein the organic molecule is serotonin.

6. The compound of claim 1, wherein the organic molecule is aminobutyric acid.

7. The compound of claim 1, wherein the organic molecule is glutamate.

8. The compound of claim 1, wherein L2 is $(R^2)_3P$.

9. The compound of claim 1, wherein L2 is trimethylphosphine.

10. The compound of claim 1, wherein L2 is triphenylphosphine.

11. A method for releasing an organic molecule from a photolabile compound, comprising:
  exposing a compound of claim 1 to light under conditions sufficient to release the organic molecule.

12. The method of claim 11, wherein the light comprises visible light or infrared light.

13. A method for protecting an organic molecule from an effect of an enzyme, comprising:
  allowing the organic molecule and a compound of Formula IVb':

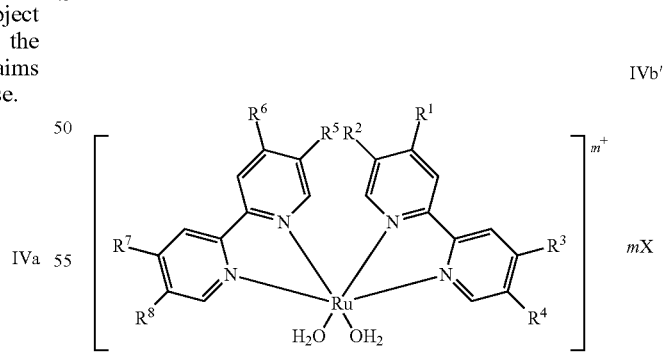

IVb' wherein m is 2; $R^1$ to $R^8$ are independently —H, —C$_1$-C$_{18}$ alkyl; —NH$_2$, —COOH, —(C$_1$-C$_{18}$ alkyl)-O—(C$_1$-C$_{18}$ alkyl), or —OC(O)(C$_1$-C$_{18}$ alkyl); and X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$,
to react under conditions sufficient to make a compound of claim 1.

14. A method for making an organic molecule bioavailable to a subject, comprising:
(a) administering a compound of claim 1 to the subject; and
(b) exposing the compound to light under conditions sufficient to release the organic molecule from the compound.

15. The method of claim 14, wherein the light is sunlight, photo-optic light, or laser light.

16. The method of claim 14, wherein the light is visible light or infrared light.

17. The method of claim 14, wherein the exposing occurs at the site of a tumor, cancer, or neoplasm.

18. The method of claim 14, wherein the administering occurs intravenously, topically, intradermally, intramuscularly, transdermally, subcutaneously, intranasally, parenterally, intrathecally, vaginally, rectally, colorectally, orally, intracranially, retroorbitally, intrasternally, or by injection.

19. A composition comprising a compound of claim 1 and a physiologically acceptable carrier, vehicle, diluent, or excipient.

20. A kit comprising a compound of claim 1 and instructions for use of the compound.

21. A method for assaying an organic molecule, comprising exposing a photolabile compound of claim 1 and a biological sample in vitro to light under conditions sufficient to release the organic molecule from the photolabile compound, and determining an effect of the organic molecule on the biological sample.

* * * * *

UNITED STATES PATENT AND TRADEMARK OFFICE
CERTIFICATE OF CORRECTION

PATENT NO. : 9,688,708 B2
APPLICATION NO. : 15/056340
DATED : June 27, 2017
INVENTOR(S) : Roberto Etchenique et al.

It is certified that error appears in the above-identified patent and that said Letters Patent is hereby corrected as shown below:

In the Specification

Column 1, Line 16, the government support clause should be changed from:
"This invention was made with government support under Grant Nos. EY011787 and EY013237 awarded by the National Institute of Health, and under Contract No. C000082 awarded by NYSTAR. The government has certain rights to the invention."

To read:
"This invention was made with government support under grants EY011787 and EY013237 awarded by the National Institutes of Health. The government has certain rights in this invention."

Signed and Sealed this
Seventh Day of November, 2017

Joseph Matal
*Performing the Functions and Duties of the*
*Under Secretary of Commerce for Intellectual Property and*
*Director of the United States Patent and Trademark Office*